(12) United States Patent
Kanzaki et al.

(10) Patent No.: US 9,272,068 B2
(45) Date of Patent: *Mar. 1, 2016

(54) PROCESS FOR PRODUCING WATER-ABSORBING RESIN

(75) Inventors: Syuji Kanzaki, Hyogo (JP); Sumio Okuda, Hyogo (JP); Kunihiko Ishizaki, Hyogo (JP); Satoshi Matsumoto, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 211 days.

This patent is subject to a terminal disclaimer.

(21) Appl. No.: 13/634,167

(22) PCT Filed: Mar. 14, 2011

(86) PCT No.: PCT/JP2011/055977
§ 371 (c)(1),
(2), (4) Date: Sep. 11, 2012

(87) PCT Pub. No.: WO2011/111856
PCT Pub. Date: Sep. 15, 2011

(65) Prior Publication Data
US 2013/0005926 A1    Jan. 3, 2013

(30) Foreign Application Priority Data

Mar. 12, 2010 (JP) .................. 2010-055236
Mar. 12, 2010 (JP) .................. 2010-055237
Mar. 12, 2010 (JP) .................. 2010-055238

(51) Int. Cl.
*C08J 3/12* (2006.01)
*A61L 15/56* (2006.01)
*A61L 15/60* (2006.01)
*C08F 6/00* (2006.01)
*B01J 20/26* (2006.01)
*C08J 3/24* (2006.01)

(52) U.S. Cl.
CPC ............... *A61L 15/56* (2013.01); *A61L 15/60* (2013.01); *B01J 20/261* (2013.01); *B01J 20/267* (2013.01); *C08F 6/008* (2013.01); *C08J 3/12* (2013.01); *C08J 3/122* (2013.01); *C08J 3/245* (2013.01); *B01J 2220/68* (2013.01); *C08J 2300/14* (2013.01); *C08J 2333/02* (2013.01)

(58) Field of Classification Search
None
See application file for complete search history.

(56) References Cited

U.S. PATENT DOCUMENTS

| 4,734,478 A | 3/1988 | Tsubakimoto et al. |
| 4,755,562 A | 7/1988 | Alexander et al. |
| 4,783,510 A | 11/1988 | Saotome |
| 4,824,901 A | 4/1989 | Alexander et al. |
| 4,893,999 A | 1/1990 | Chmelir et al. |
| 4,920,202 A | 4/1990 | Irie et al. |
| 5,005,771 A | 4/1991 | Pieh et al. |
| 5,140,076 A | 8/1992 | Hatsuda et al. |
| 5,206,205 A | 4/1993 | Tsai |
| 5,229,487 A | 7/1993 | Tsubakimoto et al. |
| 5,385,983 A | 1/1995 | Graham |
| 5,409,771 A | 4/1995 | Dahmen et al. |
| 5,422,405 A | 6/1995 | Dairoku et al. |
| 5,462,972 A | 10/1995 | Smith et al. |
| 5,597,873 A | 1/1997 | Chambers et al. |
| 5,610,208 A | 3/1997 | Dairoku et al. |
| 5,610,220 A | 3/1997 | Klimmek et al. |
| 5,633,316 A | 5/1997 | Gartner et al. |
| 5,669,894 A | 9/1997 | Goldman et al. |
| 5,672,633 A | 9/1997 | Brehm et al. |
| 5,674,633 A | 10/1997 | Saunders et al. |
| 5,945,495 A | 8/1999 | Daniel et al. |
| 5,981,070 A | 11/1999 | Ishizaki et al. |
| 6,071,976 A | 6/2000 | Dairoku et al. |
| 6,164,455 A | 12/2000 | Kakita et al. |
| 6,187,902 B1 | 2/2001 | Yanase et al. |
| 6,207,796 B1 | 3/2001 | Dairoku et al. |
| 6,228,930 B1 | 5/2001 | Dairoku et al. |
| 6,239,230 B1 | 5/2001 | Eckert et al. |
| 6,241,928 B1 | 6/2001 | Hatsuda et al. |
| 6,254,990 B1 | 7/2001 | Ishizaki et al. |
| 6,265,488 B1 | 7/2001 | Fujino et al. |
| 6,291,635 B1 | 9/2001 | Maeda et al. |
| 6,297,139 B1 | 10/2001 | Lin |
| 6,300,423 B1 | 10/2001 | Engelhardt et al. |
| 6,372,852 B2 | 4/2002 | Hitomi et al. |
| 6,388,000 B1 | 5/2002 | Irie et al. |
| 6,458,921 B1 * | 10/2002 | Dairoku et al. ............... 528/481 |
| 6,472,478 B1 | 10/2002 | Funk et al. |

(Continued)

FOREIGN PATENT DOCUMENTS

| EP | 0349240 | 1/1990 |
| EP | 0450923 | 10/1991 |
| EP | 0450924 | 10/1991 |
| EP | 0605150 | 7/1994 |
| EP | 0668080 | 8/1995 |

(Continued)

OTHER PUBLICATIONS

Chong et al; American Control Conference; 2009; 160-165.*

(Continued)

*Primary Examiner* — Robert C Boyle
(74) *Attorney, Agent, or Firm* — Dickinson Wright PLLC (57) ABSTRACT

The disclosed process for producing a water-absorbing resin comprising: a polymerization step of polymerizing an aqueous unsaturated monomer; and a drying step of drying a particulated water-containing gel-liked crosslinked polymer, obtained in a finely crushing step during the polymerization or after the polymerization. In the process, the drying step is interrupted with a dryer kept in a heated state and thereafter the drying step is restarted.

16 Claims, 1 Drawing Sheet

(56) References Cited

U.S. PATENT DOCUMENTS

| | | | |
|---|---|---|---|
| 6,503,979 B1 | 1/2003 | Funk et al. |
| 6,514,615 B1 | 2/2003 | Sun et al. |
| 6,559,239 B1 | 5/2003 | Riegel et al. |
| 6,605,673 B1 | 8/2003 | Mertens et al. |
| 6,620,889 B1 | 9/2003 | Mertens et al. |
| 6,620,899 B1 | 9/2003 | Morken et al. |
| 6,641,064 B1 | 11/2003 | Dentler et al. |
| 6,657,015 B1 | 12/2003 | Riegel et al. |
| 6,710,141 B1 | 3/2004 | Heide et al. |
| 6,716,894 B2 | 4/2004 | Kajikawa et al. |
| 6,720,389 B2 | 4/2004 | Hatsuda et al. |
| 6,727,345 B2 | 4/2004 | Kajikawa et al. |
| 6,809,158 B2 | 10/2004 | Ikeuchi et al. |
| 6,817,557 B2 | 11/2004 | Kakita et al. |
| 6,906,159 B2 | 6/2005 | Dairoku et al. |
| 6,987,151 B2 | 1/2006 | Gartner et al. |
| 7,091,253 B2 | 8/2006 | Dairoku et al. |
| 7,098,284 B2 | 8/2006 | Torii et al. |
| 7,157,141 B2 | 1/2007 | Inger et al. |
| 7,183,456 B2 | 2/2007 | Hatsuda et al. |
| 7,193,006 B2 | 3/2007 | Ishizaki et al. |
| 7,312,278 B2 | 12/2007 | Nakashima et al. |
| 7,378,453 B2 | 5/2008 | Nogi et al. |
| 7,473,739 B2 | 1/2009 | Dairoku et al. |
| 7,682,702 B2 | 3/2010 | Nitschke |
| 7,960,490 B2 | 6/2011 | Funk et al. |
| 7,967,148 B2 | 6/2011 | Stueven et al. |
| 8,071,202 B2 | 12/2011 | Furno et al. |
| 8,104,621 B2 | 1/2012 | Weismantel et al. |
| 8,138,292 B2 | 3/2012 | Matsumoto et al. |
| 8,148,485 B2* | 4/2012 | Nogi et al. ................. 526/317.1 |
| 8,188,163 B2 | 5/2012 | Matsumoto et al. |
| 2003/0020199 A1 | 1/2003 | Kajikawa et al. |
| 2003/0087983 A1 | 5/2003 | Kajikawa et al. |
| 2004/0110006 A1 | 6/2004 | Ishizaki et al. |
| 2004/0240316 A1 | 12/2004 | Nogi et al. |
| 2005/0029352 A1 | 2/2005 | Spears |
| 2005/0048221 A1 | 3/2005 | Irie et al. |
| 2005/0070671 A1 | 3/2005 | Torii et al. |
| 2005/0215734 A1 | 9/2005 | Dairoku et al. |
| 2005/0288182 A1 | 12/2005 | Torii et al. |
| 2006/0057389 A1 | 3/2006 | Reimann et al. |
| 2006/0073969 A1 | 4/2006 | Torii et al. |
| 2006/0204755 A1 | 9/2006 | Torii et al. |
| 2006/0247351 A1 | 11/2006 | Torii et al. |
| 2007/0041796 A1* | 2/2007 | Irie et al. .................... 407/30 |
| 2007/0078231 A1 | 4/2007 | Shibata et al. |
| 2007/0106013 A1 | 5/2007 | Adachi et al. |
| 2007/0123624 A1 | 5/2007 | Otten et al. |
| 2007/0141338 A1* | 6/2007 | Ishizaki et al. ............. 428/402 |
| 2007/0149691 A1* | 6/2007 | Ishizaki et al. ............. 524/500 |
| 2007/0149760 A1 | 6/2007 | Kadonaga et al. |
| 2007/0161759 A1 | 7/2007 | Riegel et al. |
| 2007/0173610 A1 | 7/2007 | Wada et al. |
| 2007/0293632 A1 | 12/2007 | Riegel et al. |
| 2008/0004408 A1 | 1/2008 | Stueven et al. |
| 2008/0021150 A1* | 1/2008 | Becker et al. .............. 524/555 |
| 2008/0202987 A1 | 8/2008 | Weismantel et al. |
| 2008/0214749 A1 | 9/2008 | Weismantel et al. |
| 2008/0221277 A1 | 9/2008 | Walden et al. |
| 2008/0280128 A1 | 11/2008 | Furno et al. |
| 2008/0287631 A1* | 11/2008 | Nitschke .................. 526/318.43 |
| 2009/0022603 A1 | 1/2009 | Feise et al. |
| 2009/0060660 A1 | 3/2009 | Funk et al. |
| 2009/0105389 A1 | 4/2009 | Walden et al. |
| 2009/0194462 A1 | 8/2009 | Stueven et al. |
| 2009/0202805 A1 | 8/2009 | Furno et al. |
| 2009/0227741 A1 | 9/2009 | Walden et al. |
| 2009/0266747 A1 | 10/2009 | Stueven et al. |
| 2009/0275470 A1 | 11/2009 | Nagasawa et al. |
| 2009/0314258 A1 | 12/2009 | Azou |
| 2009/0321682 A1 | 12/2009 | Kajikawa et al. |
| 2010/0001233 A1 | 1/2010 | Funk et al. |
| 2010/0016522 A1 | 1/2010 | Stueven et al. |
| 2010/0140546 A1 | 6/2010 | Barthel et al. |
| 2010/0249320 A1 | 9/2010 | Matsumoto et al. |
| 2011/0003926 A1 | 1/2011 | Nogi et al. |
| 2011/0006140 A1 | 1/2011 | Ishizaki et al. |
| 2011/0009590 A1 | 1/2011 | Matsumoto et al. |
| 2011/0011491 A1 | 1/2011 | Matsumoto et al. |
| 2011/0015351 A1 | 1/2011 | Nogi et al. |
| 2011/0021725 A1 | 1/2011 | Takaai et al. |
| 2011/0028670 A1 | 2/2011 | Matsumoto et al. |
| 2011/0039961 A1 | 2/2011 | Matsumoto et al. |
| 2011/0059329 A1 | 3/2011 | Dobrawa et al. |
| 2011/0088806 A1 | 4/2011 | Nogi et al. |
| 2011/0110730 A1 | 5/2011 | Nogi et al. |
| 2011/0166300 A1 | 7/2011 | Dairoku et al. |
| 2012/0157625 A1 | 6/2012 | Kitano et al. |
| 2012/0157635 A1 | 6/2012 | Nogi et al. |
| 2012/0157650 A1 | 6/2012 | Nogi et al. |
| 2012/0172536 A1 | 7/2012 | Nogi et al. |
| 2012/0220733 A1 | 8/2012 | Machida et al. |
| 2012/0220745 A1 | 8/2012 | Machida et al. |
| 2013/0281594 A1 | 10/2013 | Dobrawa et al. |
| 2014/0058346 A1 | 2/2014 | Wada et al. |

FOREIGN PATENT DOCUMENTS

| | | |
|---|---|---|
| EP | 0812873 | 12/1997 |
| EP | 1422257 | 5/2004 |
| EP | 1426402 | 6/2004 |
| EP | 2189478 | 5/2010 |
| EP | 2253375 | 11/2010 |
| EP | 2258749 | 12/2010 |
| EP | 2261148 | 12/2010 |
| EP | 2261264 | 12/2010 |
| EP | 2471843 | 7/2012 |
| EP | 2479195 | 7/2012 |
| JP | 54-053165 | 4/1979 |
| JP | 64-60683 | 3/1989 |
| JP | 1060683 | 3/1989 |
| JP | 7-224304 | 8/1995 |
| JP | 7-242709 | 9/1995 |
| JP | 7-270070 | 10/1995 |
| JP | 8-073518 | 3/1996 |
| JP | 10-059534 | 3/1998 |
| JP | 2000-063527 | 2/2000 |
| JP | 2000-143720 | 5/2000 |
| JP | 2001-018222 | 1/2001 |
| JP | 2002-226599 | 8/2002 |
| JP | 2003-012812 | 1/2003 |
| JP | 2003-082107 | 3/2003 |
| JP | 2004-197087 | 7/2004 |
| JP | 2004-345804 | 12/2004 |
| JP | 2004-352941 | 12/2004 |
| JP | 2006-160774 | 6/2006 |
| JP | 2006-198529 | 8/2006 |
| JP | 2007-224224 | 9/2007 |
| JP | 2009-256687 | 11/2009 |
| JP | 2009-545635 | 12/2009 |
| JP | 2010-053296 | 3/2010 |
| WO | 99/42494 | 8/1999 |
| WO | 99/42496 | 8/1999 |
| WO | 99/43720 | 9/1999 |
| WO | 2004/069293 | 8/2004 |
| WO | 2004/069915 | 8/2004 |
| WO | 2005/016393 | 2/2005 |
| WO | 2005/056177 | 6/2005 |
| WO | 2006/034806 | 4/2006 |
| WO | 2006/074816 | 7/2006 |
| WO | 2006/082188 | 8/2006 |
| WO | 2006/082189 | 8/2006 |
| WO | 2006/082197 | 8/2006 |
| WO | 2006/111402 | 10/2006 |
| WO | 2006/111403 | 10/2006 |
| WO | 2006/111404 | 10/2006 |
| WO | 2007/065840 | 6/2007 |
| WO | 2007/104673 | 9/2007 |
| WO | 2007/104676 | 9/2007 |
| WO | 2007/121037 | 10/2007 |
| WO | 2008/003672 | 1/2008 |
| WO | 2008/009842 | 1/2008 |
| WO | 2008/009843 | 1/2008 |

(56) References Cited

FOREIGN PATENT DOCUMENTS

| WO | 2008/015946 | | 2/2008 |
|---|---|---|---|
| WO | 2008/034786 | | 3/2008 |
| WO | 2008/037673 | | 4/2008 |
| WO | 2008/037675 | | 4/2008 |
| WO | 2008/037676 | | 4/2008 |
| WO | 2008/087114 | | 7/2008 |
| WO | 2008/123477 | | 10/2008 |
| WO | 2009/005114 | | 1/2009 |
| WO | 2009/028568 | | 3/2009 |
| WO | 2009/123193 | | 3/2009 |
| WO | 2009/113671 | | 9/2009 |
| WO | 2009/113672 | | 9/2009 |
| WO | 2009/113678 | | 9/2009 |
| WO | 2009/113679 | | 9/2009 |
| WO | WO 2009113672 A1 | * | 9/2009 |
| WO | 2009/119756 | | 10/2009 |
| WO | 2009/123197 | | 10/2009 |
| WO | 2010/032694 | | 3/2010 |
| WO | 2011/026876 | | 3/2011 |

OTHER PUBLICATIONS

International Search Report for PCT/JP2011/055977, dated May 31, 2011.
Office Action dated Feb. 13, 2013 in U.S. Appl. No. 13/634,128.
Office Action dated Jun. 20, 2013 in U.S. Appl. No. 13/578,118.
Office Action dated Sep. 24, 2013 in U.S. Appl. No. 13/634,128.
Advisory Action dated Feb. 7, 2014 in U.S. Appl. No. 13/634,128.
Notice of Reasons for Rejection, dated Nov. 26, 2013, for JP 2011-553903, and English translation thereof.
Notice of Reasons for Rejection, dated Nov. 26, 2013, for JP 2012-504554, and English translation thereof.
Notice of Reasons for Rejection, dated Nov. 26, 2013, for JP 2012-504555, and English translation thereof.
Notice of Reasons for Rejection, dated Nov. 26, 2013, for JP 2012-504556, and English translation thereof.
Office Action dated Dec. 5, 2012 in U.S. Appl. No. 13/578,118.
Office Action dated Jun. 19, 2014 issued in U.S. Appl. No. 13/578,118.
Office Action dated Jun. 27, 2014 issued in U.S. Appl. No. 13/634,128.
Office Action dated Jul. 7, 2014 issued in U.S. Appl. No. 13/634,151.
Notice of Reasons for Rejection, dated Jun. 10, 2014, in JP Application No. 2012-504555, and English translation thereof.
Advisory Action, dated Mar. 4, 2015, issued in related U.S. Appl. No. 13/634,151.
Extended European Search Report, issued Nov. 5, 2014, for EP Application No. 11742329.3.
Extended European Search Report, issued Oct. 21, 2014, for EP Application No. 11753511.2.
Extended European Search Report, issued Oct. 23, 2014, for EP Application No. 11753510.4.
Extended European Search Report, issued Oct. 17, 2014, for EP Application No. 11753512.0.
Notice of Reasons for Rejection dated Feb. 25, 2014 in JP Application No. 2012-504555, and English translation thereof.
Notice of Reasons for Rejection dated Apr. 1, 2014 in JP Application No. 2012-504556, and English translation thereof.
Notice of Reasons for Rejection dated Apr. 1, 2014 in JP Application No. 2011-553903, and English translation thereof.
Office Action dated Nov. 21, 2014 issued in related U.S. Appl. No. 13/634,151.
Final Office Action dated Mar. 3, 2015 issued in related U.S. Appl. No. 13/578,118.
Final Office Action dated Apr. 2, 2015 issued in related U.S. Appl. No. 13/634,128.
Office Action dated Apr. 17, 2015 issued in related U.S. Appl. No. 13/634,151.
Communication Pursuant to Rule 114(2) EPC, Observations by a Third Party Concerning the Patentability of the Invention, dated Oct. 8, 2015, 126 pages.
U.S. Office Action dated Sep. 28, 2015, issued for counterpart Patent Application U.S. Appl. No. 13/634,128.
European Office Action dated Nov. 11, 2015, issued for counterpart Patent Application No. 11753512.0.

* cited by examiner

PROCESS FOR PRODUCING WATER-ABSORBING RESIN

TECHNICAL FIELD

The present invention relates to a process for producing a water-absorbing resin. More concretely, the present invention relates to a method for providing a water-absorbing resin with high physical properties by uniform drying after polymerization in a process for continuously producing a water-absorbing resin in a huge scale involving joined continuous steps.

BACKGROUND ART

A water-absorbing resin (SAP/Super Absorbent Polymer) is a water-swelling and water-insoluble polymer gelling agent and has been used for mainly disposable uses including absorbing articles such as paper diapers and sanitary napkins, as well as water retention agents for agriculture and horticulture, water-stopping materials for industrial use, and the like. A large number of monomers and hydrophilic polymers have been proposed as raw materials for such a water-absorbing resin and particularly, poly(acrylic acid (salt))-type water-absorbing resins using acrylic acid and/or a salt thereof as a monomer have been industrially used most frequently owing to their high water absorbent capability.

Such a water-absorbing resin can be obtained by finely crushing a water-containing gel-like polymer, which is obtained by polymerizing an aqueous monomer solution, during or after the polymerization, and drying the obtained particulated water-containing gel-like crosslinked polymer. After drying, if necessary, a pulverizing step and a classification step are carried out and arbitrarily, the obtained product is subjected to surface-crosslinking before drying or after drying. One or more steps such as a fine powder recovery step, an undried matter removal step after drying, a packaging step, and an addition step of adding other additives (fine particles, a deodorant, an antibacterial agent, and the like) may also be carried out arbitrarily. A method to be employed as a common polymerization method is aqueous solution polymerization or reverse-phase suspension polymerization and the product form is generally a powder of about 10 to 1000 μm. Such a process for producing a water-absorbing resin involving many steps is exemplified in Patent Documents 1 to 13 or the like.

PRIOR ART DOCUMENTS

Patent Documents

Patent Document 1: WO No. 2009/113679 pamphlet
Patent Document 2: WO No. 2009/113678 pamphlet
Patent Document 3: WO No. 2009/113671 pamphlet
Patent Document 4: WO No. 2009/113672 pamphlet
Patent Document 5: WO No. 2009/119754 pamphlet
Patent Document 6: WO No. 2009/123197 pamphlet
Patent Document 7: U.S. Pat. No. 6,716,894
Patent Document 8: U.S. Pat. No. 6,727,345
Patent Document 9: U.S. Pat. No. 6,164,455
Patent Document 10: U.S. Pat. No. 6,817,557
Patent Document 11: U.S. Pat. No. 6,641,064
Patent Document 12: U.S. Pat. No. 6,291,635
Patent Document 13: EP Patent No. 1949011

SUMMARY OF THE INVENTION

Problems to be Solved by the Invention

In recent years, because of increase of the demand for paper diapers, and the like, production scale of the water-absorbing resin has been becoming wider and it leads to a tendency of scale up for one line of production apparatus and increase of polymerization concentration (increase of concentration of an aqueous monomer solution, e.g., disclosed in Patent Document 7). In order to satisfy various high levels of requests from users, a wide variety of products of water-absorbing resins have been developed. Accordingly, in the present situation, there are many steps and many additives employed after the drying step: for example, a pulverizing step, a classification step, a surface treatment step (particularly, a surface-crosslinking step), a conveying step, a granulation step, an additive addition step, a fine powder recovery step, and the like, according to the above-mentioned patent documents etc.

Therefore, the present situation is that a lot of models are produced through many steps in a single plant. The respective steps are sometimes carried out in a batch method, but in general, the main stream is a continuous process. Even if some steps are carried out in a batch method, the process in which the respective steps are joined is as a whole process, a substantially continuous process for production. In addition, substantially continuous means that even in the case of batch steps, the steps are repeatedly continuously carried out. For example, it means a state where the hydrogel or a dried material thereof is subjected to a storage step after repeated batch steps to be continuously supplied to continuous steps (even if some batch steps are involved) and these steps are regarded as continuous as a whole process.

In a process for producing a water-absorbing resin which involves many steps, the continuous flow of a water-absorbing resin or a hydrogel thereof sometimes stops in a production plant because of periodic maintenance or a temporary trouble (an operation trouble in some steps). Patent Documents 9 to 12 disclose such a trouble (stop of operation) in a crushing step, a conveying step, or a storage step.

In the case of joined steps, if even a few steps are stopped, the entire plant in which the steps are joined has to be stopped and, therefore, there occurs problems that, at the time of restarting, the quality is not stable, excess energy is required for restarting the operation, an excess load is applied to an apparatus (e.g., it can be confirmed by increase of the power consumption) and the like, and in the worst case, the operation may be stopped. In addition, a colored foreign matter (a discolored material of mainly a water-absorbing resin) may contaminate a water-absorbing resin at the time the operation is restarted.

Solutions to the Problems

To solve the above-mentioned problems, the inventors of the present invention have made earnest investigations and finally have found that the above-mentioned problems can be solved by controlling a method for stopping the drying step.

That is, the present invention (the first invention) provides a process for producing a water-absorbing resin, comprising a polymerization step of polymerizing an aqueous unsaturated monomer solution and a drying step of drying a particulated water-containing gel-like crosslinked polymer obtained in a finely crushing step during the polymerization or after the polymerization, wherein the drying step is interrupted with a dryer kept in the heated state and thereafter the drying step is restarted. Provide that, the interruption of the drying step means a state where the particulated water-containing gel-like crosslinked polymer or a dried material thereof is substantially absent in the dryer, or not charged to or not discharged out of the dryer in continuous drying.

To solve the above-mentioned problems, the present invention (the second invention) provide a process for producing a water-absorbing resin comprising a polymerization step of polymerizing an aqueous unsaturated monomer solution and a drying step of drying a particulated water-containing gel-like crosslinked polymer obtained in a finely crushing step during the polymerization or after the polymerization, wherein the drying step is interrupted and heating of a dryer is stopped, then cleaning of the inside of the dryer is started within 100 hours and thereafter the drying step is restarted. Provide that, the interruption of the drying step means a state where the particulated water-containing gel-like crosslinked polymer or a dried material thereof is substantially absent in the dryer, or not charged to or not discharged out of the dryer in continuous drying.

Effects of the Invention

In continuous production, particularly in continuous drying for drying at not less than 1 [t/hr] of a water-absorbing resin, the water-absorbing resin can be stably produced by carrying out stable drying without coloration.

MODE FOR CARRYING OUT THE INVENTION

Hereinafter, a method for producing the water-absorbing resin of the present invention will be described in detail; however, the scope of the present invention is not restricted to the following description, and those other than the following examples can be properly modified and carried out in a range where the gist of the present invention is not impaired. Specifically, the present invention is not limited to each of the following embodiments, and various modifications can be made within a range shown by the claims and embodiments carried out by properly combining each technical means disclosed with different embodiments are also included within the technical scope of the present invention.

[1] Definition of Terms (1-1) Water-Absorbing Resin

In the present invention, the "water-absorbing resin" means a water-swelling and water-insoluble polymer gelling agent. The "water-swelling" means that CRC (absorption capacity without load) defined in ERT 441.2-02 is indispensably 5 [g/g] or more and the "water-insoluble" means that Ext (extractables) defined in ERT 470.2-02 is indispensably 0 to 50 mass %.

The water-absorbing resin can be properly designed in accordance with the use and is not particularly limited, and is preferably a hydrophilic crosslinked polymer obtained by crosslinking polymerization of a carboxyl group-containing unsaturated monomer. The water-absorbing resin is not limited to the case in which the entire amount (100% by mass) is in the form of polymer, and may contain other additives and the like to the extent of retaining the above-mentioned characteristics. That is, even a water-absorbing resin composition is generally named as a water-absorbing resin in the present invention. The content of the polyacrylic acid (salt)-type water-absorbing resin is preferably 70 to 99.9 mass % relative to the entire water-absorbing resin, more preferably 80 to 99.7 mass %, and still more preferably 90 to 99.5 mass %. The components other than the water-absorbing resin are preferably water from the viewpoint of the water absorption speed and impact resistance of powder (particles) and may include, if necessary, additives described below.

(1-2) Polyacrylic Acid (Salt)-Type Water-Absorbing Resin

In the present invention, the "polyacrylic acid (salt)-type water-absorbing resin" means a water-absorbing resin having a unit derived from acrylic acid and/or a salt thereof (hereinafter, referred to as an acrylic acid (salt)) as a main repeating unit. Concretely, it means a polymer inevitably containing an acrylic acid (salt) in an amount of 50 to 100 mol %, preferably 70 to 100 mol %, more preferably 90 to 100 mol %, and particularly preferably substantially 100 mol % in the total monomers (excluding a crosslinking agent) used for polymerization. The salt as the polymer essentially contains a water-soluble salt, and preferably contains a monovalent salt, still more preferably an alkali metal salt or ammonium salt, particularly an alkali metal salt, and further sodium salt.

(1-3) Initial Color Hue and Coloration with Time

In the present invention, the "initial color hue" means the color hue of a water-absorbing resin immediately after production or immediately after shipment to users, and in general, it is controlled based on the color hue before shipment from a plant. A method for measuring the color hue may be methods (Lab value, YI value, WB value, etc.) described in WO No. 2009/005114.

The "coloration with time" means change of color hue of a water-absorbing resin caused during long time storage in an unused state or caused during distribution. Since a water-absorbing resin is colored with time, the commodity value of paper diapers may be deteriorated. The coloration with time is caused during several months to several years and, therefore, it is verified by an accelerating test (accelerating test under high temperature and high humidity) disclosed in WO No. 2009/005114.

(1-4) EDANA and ERT

The "EDANA" is an abbreviation of European Disposables and Nonwovens Associations. "ERT" is an abbreviation of measurement method (EDANA Recommended Test Method) of a water-absorbing resin on the basis of European Standards (almost Global Standards). In this specification, unless otherwise specified, the physical properties of a water-absorbing resin or the like are measured based on ERT original text (Published Literature: revised in 2002).

(a) "CRC" (ERT441.2-02)

The "CRC" is an abbreviation for Centrifuge Retention Capacity and means absorption capacity without load (simply sometimes referred to as "absorption capacity"). Specifically, the CRC is the absorption capacity (unit; g/g) after a water-absorbing resin is freely swollen in 0.9 mass % saline solution for 30 minutes, and then dehydrated in a centrifuge.

(b) "AAP" (ERT442.2-02)

The "AAP" is an abbreviation for Absorption Against Pressure and means absorption capacity under load. Specifically, the AAP is the absorption capacity (unit; g/g) in 0.9 mass % saline solution for 1 hour under a load of 2.06 kPa (0.3 psi, 21 [gf/cm$^2$]). In the present invention, the AAP was measured under a loading condition of 2.06 kPa (0.3 psi, 21 [gf/cm$^2$]) or 4.83 kPa (0.7 psi, 50 [gf/cm$^2$]).

(c) "Ext" (ERT 470.2-02)

The "Ext" is an abbreviation for Extractables and means the amount of water soluble components (amount of water-solubilized components). Specifically, measurement is carried out by adding 1 g of the water-absorbing resin to 200 g of an 0.9 mass % aqueous saline solution, stirring the solution for 16 hours, and measuring the amount of a dissolved polymer by pH titration (unit: mass %).

(d) "FSC" (ERT440.2-02)

The "FSC" is an abbreviation of Free Swell Capacity and means the ratio of free swelling. Concretely, it is the absorption capacity (unit; [g/g]) measured by immersing 0.20 g of a water-absorbing resin in an aqueous solution of 0.9 mass % of sodium chloride for 30 minutes and carrying out the measurement without dehydration by a centrifuge.

(e) "Residual Monomers" (ERT410.2-02)

The "Residual Monomers" means the amount of monomers remaining in a water-absorbing resin. Specifically, the amount of monomers is a value (unit; ppm by mass) obtained by measuring, after 0.5 g of a water-absorbing resin is charged to 0.9 mass % saline solution and the resultant is stirred for 2 hours, the amount of monomers eluted in the aqueous solution by using high-pressure liquid chromatography.

(f) "PSD" (ERT420.2-02)

The "PSD" is an abbreviation for Particle Size Distribution and means the particle size distribution measured by sieving classification. The mass average particle diameter (D50) and the particle diameter distribution width can be measured by the same method as in "(1) Average Particle Diameter and Distribution of Particle Diameter" described in European Patent No. 0349240, p. 7, lines 25-43.

(g) Other Physical Properties of Water-Absorbing Resin Defined in EDANA

"pH" (ERT400.2-02): The "pH" means pH of a water-absorbing resin.

"Moisture Content" (ERT 430.2-02): The moisture content means the water content percentage of a water-absorbing resin.

"Flow Rate" (ERT 450.2-02): The flow rate means the flow down speed of a water-absorbing resin.

"Density" (ERT 460.2-02): The density means the bulk specific density of a water-absorbing resin.

"Respirable Particles" (ERT 480.2-02): The respirable particles mean the respirable dust of a water-absorbing resin.

"Dust" (ERT 490.2-02): The dust means the dust contained in a water-absorbing resin.

(1-5) Liquid Permeability

The "liquid permeability" means the flow of a liquid flowing among particles of swollen gel under a load or without a load. The "liquid permeability" can be measured by SFC (Saline Flow Conductivity) or GBP (Gel Bed Permeability) as a representative measurement method.

The "SFC (saline flow conductivity)" means the liquid permeability of 0.9 g of a water-absorbing resin at a load of 0.3 psi for an aqueous solution of 0.69 mass % of sodium chloride. It is measured according to an SFC testing method described in U.S. Pat. No. 5,669,894.

The "GBP" means the liquid permeability of a water-absorbing resin under a load or free expansion for 0.69 mass % physiological saline solution. It is measured according to a GBP testing method described in WO No. 2005/016393 pamphlet.

(1-6) Heating State of an Apparatus

The "heating state of an apparatus" in the present invention means a state where an apparatus is heated with a heat source such as an electric heater, steam, or hot air, but does not mean a state where the apparatus is kept warm with residual heat after the heat source is turned off. It includes a state where the heat source is turned off for controlling the temperature constant. The apparatus means an apparatus employed in the respective steps and examples thereof include a dryer in a drying step and a heating treatment apparatus in a surface treatment (crosslinking) step.

(1-7) Interruption of Steps

In the present invention, the "interruption of steps" means a state where a particulated water-containing gel-like crosslinked polymer, a dried material thereof, or a water-absorbing resin powder is substantially absent in an apparatus or not charged to or not discharged out of an apparatus in continuous steps. That is, the "substantially absent state" means that a particulated water-containing gel-like crosslinked polymer, a dried material thereof, or a water-absorbing resin powder, which is in a state of being able to be taken out of an apparatus, is taken out of the apparatus (generally in an amount of not less than 95 mass % in the entire retention capability of the apparatus, preferably not less than 98 mass %, still more preferably not less than 99 mass %, and particularly preferably substantially 100 mass %). A small amount of the particulated water-containing gel-like crosslinked polymer, the dried material thereof, or the water-absorbing resin powder may be deposited, dropped, retained, or scattered in the apparatus. In addition, an idling operation of the apparatus is also included in the "interruption of steps" in the present invention. In the continuous steps, "a state not charged to or discharged out of an apparatus" means a state where a particulated water-containing gel-like crosslinked polymer, a dried material thereof, or a water-absorbing resin powder is stopped in an apparatus and a state where the apparatus is stopped.

(1-8) Continuous Production Such as Continuous Polymerization and Continuous Drying In the present invention, "continuous production such as continuous polymerization and continuous drying" means a state where the water-absorbing resin is continuously charged to and continuously discharged out of an apparatus in the respective steps, the present invention is preferably applied such continuous production (in respective steps of drying, surface-crosslinking, etc.) for an operation time (duration) of preferably not shorter than 24 hours, more preferably not shorter than 240 hours (10 days), and still more preferably not shorter than 720 hours (30 days).

(1-9) Others

In this description, "X to Y" showing a range means "not less than X and not more than Y". Additionally, the unit of mass "t (ton)" means "Metric ton" and unless otherwise specified, "ppm" means "ppm by weight" or "ppm by mass". Additionally, " . . . acid (salt)" means " . . . acid and/or a salt thereof" and "(meth)acrylic" means "acrylic and/or methacrylic".

[2] Process for Producing Water-Absorbing Resin (2-1) Polymerization Step

This step is a step of obtaining a water-containing gel-like crosslinked polymer by polymerizing an aqueous solution containing acrylic acid and/or a salt thereof (hereinafter, referred to as an "acrylic acid (salt)" as a main component.

(a) Monomer (Excluding Crosslinking Agent)

A water-absorbing resin to be obtained by the present invention is produced by using, as a raw material (monomer), an aqueous solution containing an acrylic acid (salt) as a main component and generally polymerized in an aqueous solution state. The monomer concentration (solid content concentration) of the aqueous monomer solution is generally 10 to 90 mass % and preferably 20 to 80 mass %. Polymerization with a high monomer concentration (not lower than 35 mass %, still more preferably not lower than 40 mass %, particularly preferably not lower than 45 mass %, and the saturated concentration as the upper limit, still more preferably not higher than 80 mass % and particularly preferably not higher than 70 mass %) is one of most preferable examples.

In the case a monomer is polymerized in an aqueous solution state, if necessary, surfactants, polymer compounds such as a polyacrylic acid (salt), starch, cellulose, and polyvinyl alcohol, various kinds of chelating agents, and various kinds of additives may be added in an amount of 0 to 30 mass % relative to the monomer.

The hydrogel obtained by the polymerization of the aqueous solution, preferably has at least partially neutralized acid groups in the polymer from the viewpoint of water absorption properties. The neutralization may be carried out before polymerization (monomer), during polymerization, or after polymerization (hydrogel) of acrylic acid and from the viewpoint of improvement of the productivity of the water-absorbing resin, AAP (absorption capacity under load), SFC (saline flow conductivity), and the like, it is preferable to carry out neutralization before polymerization of acrylic acid. That is, it is preferable to use neutralized acrylic acid (that is, a partially neutralized salt of acrylic acid) as a monomer.

The neutralization ratio of the neutralization is not particularly limited and it is preferably 10 to 100 mol %, more preferably 30 to 95 mol %, still more preferably 50 to 90 mol %, and particularly more preferably 60 to 80 mol % of the acid group. In the case the neutralization ratio is less than 10 mol %, particularly CRC (absorption capacity without load) is sometimes considerably lowered and, therefore, it is not preferable.

In the case an acrylic acid (salt) is used as a main component in the present invention, hydrophilic or hydrophobic unsaturated monomers (hereinafter, sometimes also referred to as "other monomers") may be used besides an acrylic acid (salt). The other monomers is not particularly limited and may include methacrylic acid, maleic acid, maleic anhydride, 2-(meth)acrylamido-2-methylpropanesulfonic acid, (meth)acryloxyalkanesulfonic acid, N-vinyl-2-pyrrolidone, N-vinylacetamide, (meth)acrylamide, N-isopropyl(meth)acrylamide, N,N-dimethyl(meth)acrylamide, 2-hydroxyethyl (meth)acrylate, methoxypolyethylene glycol (meth)acrylate, polyethylene glycol (meth)acrylate, stearyl acrylate, their salts, etc. In the case these other monomers are used, their use amount is not particularly limited as long as the water absorption property of the water-absorbing resin to be obtained is not deteriorated and it is preferably not more than 50 mass % and more preferably not more than 20 mass % relative to the total weight of the monomers.

(b) Salt for Neutralization

A basic substance to be used for neutralizing acrylic acid as a monomer or a polymer (hydrogel) after the polymerization is not particularly limited and is preferably monovalent basic substances, for example, alkali metal hydroxides such as sodium hydroxide, potassium hydroxide, lithium hydroxide and the like, and (hydrogen) carbonate salts such as sodium (hydrogen) carbonate, potassium (hydrogen) carbonate and the like, and is particularly preferably sodium hydroxide. The temperature at the time of neutralization (neutralization temperature) is also not particularly limited and preferably 10 to 100° C. and more preferably 30 to 90° C. Regarding the neutralization treatment conditions and the like, other than the above-mentioned ones, the conditions and the like, disclosed in WO No. 2006/522181 and U.S. Pat. No. 6,388,000 are preferably employed in the present invention.

(c) Crosslinking Agent (Internal Crosslinking Agent)

In the present invention, from the viewpoint of water absorption properties of the water-absorbing resin to be obtained, it is particularly preferable to use a crosslinking agent (hereinafter, sometimes referred to as an "internal crosslinking agent"). An internal crosslinking agent to be used may be compounds having 2 or more polymerizable double bonds in one molecule and polyfunctional compounds having 2 or more functional groups capable of forming covalent bonds by reaction with a carboxyl group in one molecule. For examples, one or more kinds of polymerizable crosslinking agents with the acrylic acid, reactive crosslinking agents with a carboxyl group, and crosslinking agents having both of these properties can be exemplified. Concrete examples are, as a polymerizable crosslinking agent, compounds having at least two polymerizable double bonds in a molecule such as N,N'-methylene bisacrylamide, (poly)ethylene glycol di(meth)acrylate, (polyoxyethylene)trimethylolpropane tri(meth)acrylate, and poly(meth)allyloxyalkanes. Further, examples of the reactive crosslinking agent are covalent-binding crosslinking agents, for example polyglycidyl ether such as ethylene glycol diglycidyl ether, poly alcohols such as propanediol, glycerin, sorbitol and the like, and ion-binding crosslinking agents such as polyvalent metal compounds of aluminum salt and the like. Among these crosslinking agents, from the viewpoint of water absorbent properties, polymerizable crosslinking agents with the acrylic acid, particularly, acrylate type, allyl type, and acrylamide type polymerizable crosslinking agents are preferably used. These internal crosslinking agents may be used alone or two or more kinds of them may be used in combination. The use amount of the internal crosslinking agent is preferably 0.001 to 5 mol %, more preferably 0.005 to 2 mol %, still more preferably 0.01 to 1 mol %, and particularly preferably 0.03 to 0.5 mol % relative to the monomer excluding the crosslinking agent from the viewpoint of physical property.

(d) Other Minor Components

In the present invention, from the viewpoint of color hue stability and residual monomers, the content of protoanemonin and/or furfural in acrylic acid is preferably 0 to 10 ppm, more preferably 0 to 5 ppm, and still more preferably 0 to 1 ppm. For the same reason, the content of an aldehyde component other than furfural and/or maleic acid in acrylic acid is preferably 0 to 5 ppm, more preferably 0 to 3 ppm, still more preferably 0 to 1 ppm, and particularly preferably 0 ppm (under detection limit). Examples of the aldehyde component other than furfural include benzaldehyde, acrolein, acetaldehyde and the like. In order to reduce the residual monomers, the content of acrylic acid dimer is preferably 0 to 500 ppm, more preferably 0 to 200 ppm, and still more preferably 0 to 100 ppm.

In the present invention, from the viewpoint of polymerization stability, it is preferable to include methoxyphenols in the unsaturated monomers and it is more preferable to include p-methoxyphenol. The content of methoxyphenols is preferably 1 to 250 ppm, more preferably 5 to 200 ppm, still more preferably 10 to 160 ppm, and particularly preferably 20 to 100 ppm relative to the monomer (acrylic acid).

(e) Other Components in Aqueous Monomer Solution

In order to improve various physical properties of the water-absorbing resin to be obtained by the present invention, the following substances may be added as arbitrary components to the aqueous monomer solution. That is, a water-soluble resin or a water-absorbing resin such as starch, a polyacrylic acid (salt), polyvinyl alcohol, or polyethylene imine may be added in an amount of, for example, 0 to 50 mass %, preferably 0 to 20 mass %, more preferably 0 to 10 mass %, and still more preferably 0 to 3 mass % relative to the monomer. Further, additives such as various kinds of foaming agents (carbonates, azo compounds, air bubbles, etc.), surfactants, various kinds of chelating agents, hydroxycarboxylic acids, and reducing inorganic salts may be added in an amount of, for example, 0 to 5 mass % and preferably 0 to 1 mass % relative to the monomer.

Among them, in the case of aiming at suppression of coloration with the time (improvement of color hue stability at the time of long time storage under high temperature and high humidity) and improvement of urine resistance (gel deterioration prevention) of the water-absorbing resin, a chelating agent, a hydroxycarboxylic acid, and a reducing inorganic salt are preferably used and a chelating agent is particularly preferably used. The use amount in this case is preferably 10 to 5000 ppm, more preferably 10 to 1000 ppm, still more preferably 50 to 1000 ppm, and particularly preferably 100 to 1000 ppm relative to the water-absorbing resin. The compounds disclosed in WO No. 2009/005114 and EU Patent Application Publication Nos. 2057228 and 1848758 may be used for the chelating agent, hydroxycarboxylic acid, and reducing inorganic salt.

(f) Polymerization Initiator

A polymerization initiator to be used for the present invention is not particularly limited and can be selected properly in accordance with the polymerization mode. Examples of the polymerization initiator may include a heat decomposition type polymerization initiator, a photodecomposition type polymerization initiator, a redox type polymerization initiator, and the like. Examples of the heat decomposition type polymerization initiator may include persulfate such as sodium persulfate, potassium persulfate, and ammonium persulfate; peroxides such as hydrogen peroxide, tert-butyl peroxide, and methyl ethyl ketone peroxide; azo compounds such as 2,2'-azobis(2-amindinopropane)dihydrochloride, 2,2'-azobis[2-(2-imidazolin-2-yl)propane]dihydrochloride, and the like. Examples of the photodecomposition type polymerization initiator may include benzoin derivatives, benzyl derivatives, acetophenone derivatives, benzophenone derivatives, azo compounds, and the like. Examples of the redox type polymerization initiator may include the above-mentioned persulfate or peroxides in combination with reducing compounds such as L-ascorbic acid and sodium hydrogen sulfite. Further, combination use of a heat decomposition type polymerization initiator and a photodecomposition type polymerization initiator can also be exemplified as a preferable embodiment. The use amount of those polymerization initiators is preferably 0.0001 to 1 mol % and more preferably 0.001 to 0.5 mol % relative to the monomer. In the case the use amount of a polymerization initiator exceeds 1 mol %, it may cause coloration of the water-absorbing resin and, therefore, it is not preferable. On the other hand, if the use amount of a polymerization initiator is below 0.0001 mol %, it may possibly increase the residual monomer amount and, therefore, it is not preferable.

In place of use of the polymerization initiator, polymerization may be carried out by irradiation with an active energy beam such as radiation beam, electron beam, or ultraviolet rays and also polymerization may be carried out by employing the active energy beam and a polymerization initiator in combination.

(g) Polymerization Method (Crosslinking Polymerization Step)

In the present invention, from the viewpoint of water absorption properties of a water-absorbing resin to be obtained, ease of polymerization control in the case of polymerization of the aqueous monomer solution, and the like, generally, aqueous solution polymerization or reverse-phase suspension polymerization is employed, and aqueous solution polymerization is preferable and continuous aqueous solution polymerization is more preferably employed. Among them, continuous aqueous solution polymerization is preferably employed for production of a water-absorbing resin in a huge scale with a large production amount for one line. The production amount is 0.5 [t/hr] or higher, more preferably 1 [t/hr] or higher, still more preferably 5 [t/hr] or higher, and particularly preferably 10 [t/hr] or higher.

Examples of a preferable embodiment of the continuous aqueous solution polymerization include continuous belt polymerization (U.S. Pat. Nos. 4,893,999, 6,241,928, US Patent Application Publication No. 2005/215734, etc.) and continuous kneader polymerization (U.S. Pat. Nos. 6,987,151, 670,141, etc.).

One of most preferable examples of the continuous aqueous solution polymerization is high temperature starting polymerization at a polymerization starting temperature of not lower than 30° C., preferably not lower than 35° C., more preferably not lower than 40° C., still more preferably not lower than 50° C., and particularly preferably not lower than 60° C. (upper limit is boiling point) or high monomer concentration polymerization with a monomer concentration of not lower than 35 mass %, preferably not lower than 40 mass %, and particularly preferably not lower than 45 mass % (upper limit is the saturated concentration). The polymerization starting temperature is defined in accordance with the liquid temperature of an aqueous monomer solution immediately before the solution is supplied to a polymerization apparatus, the conditions, and the like, disclosed in U.S. Pat. Nos. 6,906,159, 7,091,253, etc. can be employed preferably for the present invention.

From the viewpoint of improvement of physical property of the water-absorbing resin to be obtained and drying efficiency, it is preferable to evaporate water at the time of polymerization and obtain a water-absorbing resin with a higher solid content concentration. The increase degree of the solid content from the aqueous monomer solution (solid content of hydrogel after polymerization—solid content of monomer before polymerization) is preferably not less than 1 mass %, more preferably 2 to 40 mass %, and still more preferably 3 to 30 mass %. The increase degree is preferably within a range of giving a water-containing gel-like crosslinked polymer containing not more than 80 mass % of solid content.

The polymerization can be carried out in atmospheric air; however, from the viewpoint of prevention of coloration, it is preferable to carry out the polymerization in an inert gas atmosphere of nitrogen, argon, and the like (e.g., with not more than 1% by volume of oxygen concentration). It is also preferable to carry out the polymerization after replacing the dissolved oxygen in a monomer or a solution containing a monomer with an inert gas (e.g., dissolved oxygen concentration; less than 1 mg/L). The polymerization can be carried out under any pressure; that is, under reduced pressure, under normal pressure, or under pressurization.

(2-2) Finely Crushing Step of Water-Containing Gel-Like Crosslinked Polymer (Gel-Crushing Step)

This step is a step of finely crushing a water-containing gel-like crosslinked polymer obtained in the polymerization step to obtain a particulated water-containing gel-like crosslinked polymer (hereinafter, referred to as a "particulated hydrogel").

The hydrogel obtained in the polymerization step may be dried as it is, but in order to solve the above-mentioned problems, the hydrogel may be gel-crushed, if necessary, preferably during the polymerization or after the polymerization by a crusher (a kneader, a meat chopper, a cutter mill, etc.) to be particulate. That is, between the polymerization step by the continuous belt polymerization or the continuous kneader polymerization and the drying step, a step of finely crushing of the hydrogel (hereinafter, also referred to as "gel-crushing") may be added further. In addition, even in the case the gel is finely crushed by dispersion in a solvent at the time of polymerization such as reverse-phase suspension polymerization, the finely crushing step (finely crushing during polymerization) is included in the finely crushing step of the present invention, and the finely crushing is preferably carried out using a crusher.

The temperature of the hydrogel at the time of gel-crushing is kept at or increased to preferably 40 to 95° C. and more preferably 50 to 80° C. from the viewpoint of physical properties. The mass average particle diameter (D50) of the particulated hydrogel after the gel-crushing is preferably 0.5 to 4 mm, more preferably 0.3 to 3 mm, and still more preferably 0.5 to 2 mm. If the mass average particle diameter (D50) of the particulated hydrogel is within the above-mentioned range, drying is efficiently carried out and, therefore, it is preferable. The ratio of the particulated hydrogel having a particle diameter of not smaller than 5 mm is preferably 0 to 10 mass % and more preferably 0 to 5 mass % in the entire particulated hydrogel. Herein, the particle diameter of the particulated hydrogel is measured by a wet classification method described in paragraph [0091] in JP-A-2000-63527.

(2-3) Drying Step

Figure 1:
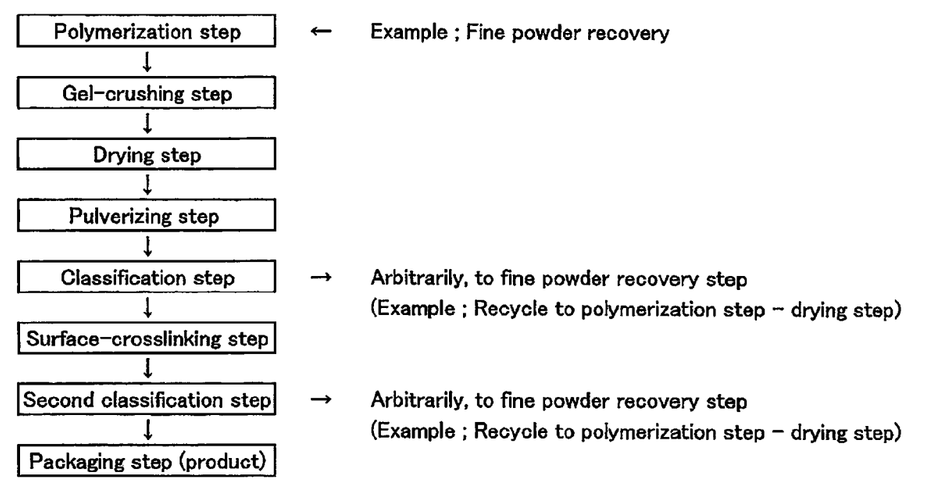
FIG. 1 is a schematic view showing the typical continuous production flow of a water-absorbing resin.

The process for producing a water-absorbing resin of the present invention is a process for producing a water-absorbing resin involving a polymerization step of polymerizing an aqueous unsaturated monomer solution, a drying step of drying a particulated water-containing gel-like crosslinked polymer obtained in a finely crushing step during the polymerization or after the polymerization, and thereafter, if necessary, a pulverizing step after drying, a classification step after drying, a surface treatment step for a water-absorbing resin powder after the classification step, and a second classification step after the surface treatment step (e.g., see FIG. 1) and is characterized in that the drying step is interrupted with a dryer kept in the heated state and thereafter the drying step is restarted. The "interruption of drying step" means a state where the particulated water-containing gel-like crosslinked polymer, or a dried material thereof is substantially absent in a dryer or not charged to or not discharged out of a dryer in continuous drying step.

The step of producing a water-absorbing resin involves a large number of steps such as a polymerization step, a finely crushing step, and a drying step, which are carried out in continuous operation; however, in the present invention, it is assumed that the drying step is interrupted.

That is, in the present invention, the inventors paid attention to a method for stopping a dryer and have found that the dryer can be smoothly operated at the time of restarting and continuous drying can be carried out stably without contamination of colored matter by keeping the dryer in a heated state even in a interruption period of the drying step. "Keeping the dryer in a heated state" means consecutive supply of a heat source and a heated state based only on remaining heat without supply of a heat source during the stop period of the dryer is not included in the heated state.

Examples of the heat source include an electric heater, and various kinds of heated gases such as steam and hot air, and consecutive supply of heated gas is preferable. Heated steam (not lower than 100° C.) is particularly preferably used as a heat source. The heated steam is recycled and reheated through a heat exchanger if necessary, and used in the drying step of the water-absorbing resin or in another step. The consecutive supply of a heat source to the dryer may be carried out so as to give a desired heating temperature or preferably keep a temperature range as described below and it may be continuous heating or intermittent heating (On/Off). The heating temperature may be constant or fluctuated.

The dryer, the particulated water-containing gel-like crosslinked polymer remaining in the dryer, and a dried material thereof are heated preferably by a method of blowing air heated by the heat source into the dryer, or by a method of warming the dryer by tracing. In the case the particulated water-containing gel-like crosslinked polymer having a solid content of not more than 80 mass %, or further not more than 70 mass %, or particularly not more than 50 mass % remains in the dryer, the polymer tends to adhere to the dryer and increase the load on starting of a belt in the dryer, and sometimes cannot be separated from the belt. Further, since the particulated water-containing gel-like crosslinked polymer tends to form large agglomerates which are difficult to be dried or pulverized, a load is applied to the dryer, a pulverizer etc. at the time of restarting and it may sometimes result in stopping again. Consequently, the particulated water-containing gel-like crosslinked polymer is preferably dried by heating during the interruption period of the drying step.

Herein, the drying step may be carried out in any of a continuous manner, a semi-continuous manner, and a batch manner in the present invention and among them, a continuous drying step is preferably employed. That is, at the time of stopping the continuous drying step, the dryer is stopped while being kept hot and thereafter the drying is restarted. If drying is restarted after the dryer is stopped completely, excess energy (torque) is needed at the time of starting the operation, particularly, starting the belt or a colored foreign matter may be mixed.

Regarding the steps before and after the continuous drying step, these steps are also preferably continuous steps or substantially continuous steps, and preferably a continuous polymerization step, a continuous pulverizing step, and a continuous classification step. The "substantially continuous step" means that even batch steps are continuously repeated, and, for example, even if some batch steps are included in the production process by setting a storage step for a hydrogel and a dried material thereof after the batch steps and continuously supplying the hydrogel and the dried material thereof to a continuous step, the process as a whole can be a continuous step.

Various kinds of dryers can be used as the dryer to be used in the drying step in the present invention without any particular limitation. An air ventilating band type continuous dryer and a fluidized bed dryer are preferably used and an air ventilating band type continuous dryer is still more preferably used. The air ventilating band type continuous dryer can efficiently carry out drying and is most effective during the interruption in a heated state in the present invention. Examples of the air circulation band type dryer are disclosed in Patent Documents 1 to 5.

As for the operation time of the drying, continuous drying is carried out preferably for not shorter than 24 hours, more preferably for not shorter than 120 hours, still more preferably for not shorter than 240 hours, and particularly preferably for not shorter than 720 hours. The time from stopping of drying to starting of drying (the interruption period of the drying step in the present invention) is preferably not shorter than 0.5 hours, more preferably not shorter than 0.5 hours and within 100 days, still more preferably not shorter than 1 hour and within 50 days, particularly preferably not shorter than 5 hours and within 20 days, and most preferably not shorter than 10 hours and within 15 days. In the case the interruption period of the drying step is shorter than 0.5 hours, since the amount of temperature decrease from the drying temperature before stopping is small, the effect of stopping in the heated state is small. On the other hand, in the case the interruption period of the drying step exceeds 100 days, since the dryer is not used for a long period, the energy use continues for a long period and it results in disadvantage of the energy cost.

The temperature of the dryer (atmosphere temperature in the dryer) during the interruption period of the drying step is not particularly limited as long as the heated state is continued and from the viewpoint of the energy and coloration issue, the temperature is preferably lower than the drying temperature and concretely, it is lower than the drying temperature preferably by not less than 10° C., and more preferably by not less than 20° C., not less than 30° C., and not less than 40° C. in this order. The temperature of the dryer during the interruption of the drying step is preferably not lower than 40° C., more preferably not lower than 50° C., and still more preferably not lower than 60° C. If the temperature of the dryer is lower than 40° C., excess energy is needed at the time of starting the belt and a colored foreign matter derived from substances adhering to the belt may be mixed at the time of restarting of the drying step and, therefore, it is undesirable. Further, in the case the particulated water-containing gel-like crosslinked polymer or a dried material thereof remains in the dryer, its separation from the belt is impossible and the polymer or a dried material thereof forms agglomerates difficult to be dried and pulverized, resulting in an undesirable consequence, that is, stopping of the drying step and the pulverizing step may be caused again. In the case a punching metal or a metal net described later is used for the belt, the belt may be clogged to deteriorate the drying efficiency in some cases. Consequently, the temperature of the dryer during the interruption period of the drying step is not lower than 40° C., more preferably not lower than 60° C., and still more preferably 80 to 140° C.

It is preferable that retained substance (or its particles) of the particulated water-containing gel-like crosslinked polymer or a dried material thereof is removed from the dryer during the interruption period of the drying step. Removal of the retained substance (including the dropped retained substance) gives the water-absorbing resin free from a colored foreign matter (e.g., the water-absorbing resin burned out to be yellow, brown, dark brown, or black). The colored foreign matter is produced by long time retention of the retained substance of the particulated water-containing gel-like crosslinked polymer or a dried material thereof in the dryer. Consequently, in the case of continuous operation for not shorter than 5 days, not shorter than 10 days, or furthermore not shorter than 20 days, it is preferable to periodically remove and clean up the retained substance of the particulated water-containing gel-like crosslinked polymer or a dried material thereof. The form of the retained substance is not particularly limited, but it is generally particulate, and its particles are retained in the dryer by dropping from the air ventilating belt of the dryer, scattering, or adhering to the dryer. A method for removing the retained substance may be vacuum suction, removal by a brush, or blowing up with (pressurized) air. At the time of removal of (particles of) the retained substance from the dryer, the dryer may be in the heated state; however, in the case a worker cleans the inside of the dryer, from the viewpoint of the ease of the removal work, it is preferable to quickly carry out the cleaning work after the temperature is decreased to around room temperature. That is, after the heating by the dryer is stopped, cleaning may be started within 100 hours. Cleaning is started preferably within 48 hours, more preferably within 24 hours, still more preferably within 12 hours, and particularly preferably within 6 hours. If times passes while the heating is stopped, adhesion of the retained substance becomes intense as described above and the cleaning may become difficult.

(a) Dryer

A dryer to be used in the present invention is preferably an air ventilating belt type dryer (belt type dryer) and also, if necessary, one or more kinds of a heat conduction and heat transfer type dryer, a radiation heat transfer type dryer, a hot air heat transfer type dryer, an induction heating type dryer, etc. may be used and from the viewpoint of quick drying, a hot air heat transfer type dryer (hereinafter, referred to as a hot air dryer) is preferable. Examples of the hot air dryer include an air ventilating belt (band) type, air ventilating circuit type, air ventilating vertical type, parallel flow belt (band) type, air ventilating tunnel type, air ventilating groove stirring type, fluidized bed type, current type, spraying type dryers and the like, and in the present invention, from the viewpoint of the physical property control, an air ventilating belt type dryer is preferable. It is possible to use another dryer in combination, but it is preferable to carry out drying by solely the air ventilating belt type dryer (belt type dryer).

The drying temperature is in a temperature range (hot air temperature) of generally 100 to 250° C., preferably 100 to 220° C., more preferably 120 to 200° C., and particularly preferably 150 to 190° C. It is more efficient that the velocity of the hot air passing in a drying chamber is higher in a range of scarcely blowing out the polymer and the velocity is preferably 0.1 to 5 [m/s] and more preferably 0.5 to 3 [m/s]. If the velocity is below 0.1 [m/s], it takes such a long time to dry out to a prescribed moisture content that a huge dryer is required. On the other hand, if the velocity exceeds 5 [m/s], the amount of the polymer flying out of the drying chamber is increased and stable operation becomes difficult. The drying time (the time from charging of the particluated water-containing gel-like crosslinked polymer to the dryer to discharge of the same particluated water-containing gel-like crosslinked polymer in form of a dried material out of the dryer) depends on the surface area and moisture content of the polymer, the type of the dryer, and the air blow quantity and is selected to give an intended moisture content. For example, the drying time is properly selected in a range of preferably 0.05 to 3 hours, more preferably 0.1 to 2 hours, and still more preferably 0.2 to 1 hour.

The present invention is applied for huge scale continuous drying with a belt length of the dryer in a range of 5 to 100 m, further 10 to 70 m, and particularly 20 to 60 m. The width of the belt is not particularly limited and it is properly determined in a range of generally 0.5 to 10 m and further preferably 1 to 5 m. The ratio between the width direction and the longitudinal direction may be determined in accordance with the purpose, but it is preferably longer in the longitudinal direction (proceeding direction) than in the width direction and the ratio is properly determined in a range of generally 3 to 500 times and further 5 to 100 times.

The drying in the present invention is preferably carried out on a continuous air ventilating belt and examples of the air ventilating belt include a metal net (e.g., meshes of 1000 to 45 μm) and a punching metal and a punching metal is preferably used. The shape of holes of a punching metal may be various and examples thereof include round holes, elliptic holes, rectangular holes, hexagonal holes, long round holes, long rectangular holes, diamond holes, cross holes, and a plurality of these holes in combination and the arrangement of the holes may be in zigzag or in parallel arrangement. The belt may have holes formed three-dimensionally like louvers but preferably have holes in a flat structure. The pitch direction of the belt may be vertical, transverse, or slanting to the belt proceeding direction and may be a combination of these. The size of the holes and hole ratio of the punching metal will be described later.

The conveying speed of the particulated water-containing gel-like crosslinked polymer on the air ventilating belt may be properly adjusted in accordance with the belt width, the belt length, the production amount, and the drying time and from the viewpoint of the load to the belt driving apparatus, durability and the like, it is preferably 0.3 to 5 [m/min], more preferably 0.5 to 2.5 [m/min], still more preferably 0.5 to 2 [m/min], and particularly preferably 0.7 to 1.5 [m/min].

In order to achieve the present invention, it is preferable to change the temperature, dew point, and air blow quantity in multi-stages and therefore, the air ventilating belt type dryer preferably has not less than 5 chambers, particularly not less than 6 chambers, and further not less than 8 chambers. The upper limit may be properly set in accordance with the scale or the like, and generally about 20 chambers suffice.

(b) Surface Occupancy

In the production process of the present invention, in the case an air ventilating band dryer is used, the surface occupancy on the belt is generally 85 to 100%, preferably 87 to 100%, more preferably 87 to 99%, particularly preferably 90 to 98%, and most preferably 93 to 97%. The surface occupancy is defined as the area ratio (percentage) of the layered material of the particulated hydrogel occupying the air ventilating belt face to the air ventilating belt area (A) in the initial period of the drying step. The air ventilating belt area (A) includes the areas of the holes. The area (B) of the air ventilating belt face on which the layered material of the particulated hydrogel in the initial drying period occupies is defined by the occupying area of the layered material of the particulated hydrogel in the section. The surface occupancy (B/A× 100(%)) is defined by the air ventilating belt area (A) that is defined aforementioned and the area (B) occupied by the layered material of the particulated hydrogel. If the surface occupancy exceeds 99% or less than 85%, it is found that the physical properties of a water-absorbing resin tend to be deteriorated and the dropping and scattering ratio, drying efficiency, and continuous drying property tend to be lowered. Unoccupied places on the belt may be properly determined and parts where no hydrogel is layered may be formed in certain set positions in the center part, both end parts, and middle parts and preferably a prescribed region where no hydrogel is set is formed in both end parts.

(c) Hole Ratio and Holes

In the production process of the present invention, in the case an air ventilating band dryer is used, the hole ratio of the punching metal is preferably 15 to 50%, more preferably 20 to 45%, and particularly preferably 25 to 40%. The hole ratio is determined in accordance with the holes, pitches (P) and the like, and in the case there is no hole in a certain prescribed region, for example, the punching metal has rims, the hole ratio is defined based on the area including the region. If the hole ratio is out of the above-mentioned range, it is found that the physical properties of a water-absorbing resin tend to be deteriorated and the drying efficiency and continuous drying property tend to be lowered.

The area of one hole (in the case where there are a plurality of types of holes, the area is defined as an average opening area) is preferably larger than the cross-sectional area of one particle of the particulated hydrogel, more preferably in a range of 2 to 100 times as large, and still more preferably in a range of 4 to 50 times as large. The maximum opening distance of each hole (e.g., the diameter in the case of a circle, or the longer diameter in the case of an ellipse) is preferably larger than the mass average particle diameter of the particulated hydrogel, more preferably in a range of 2 to 100 times as large, and still more preferably in a range of 4 to 50 times as large. The average opening area of the holes is 5 to 500 mm$^2$, preferably 10 to 100 mm$^2$, and particularly preferably 15 to 50 mm$^2$. In the case the area is smaller than the above-mentioned range, the drying efficiency is lowered and in the case it is larger, the yield of the dried material is lowered and therefore, these cases are not preferable.

(d) Resin Solid Content

As described above, in the polymerization step in the production process of the present invention, continuous kneader polymerization or continuous belt polymerization, which is carried out while evaporating water, is preferable. In this polymerization step, the increase degree of the solid content (the difference between the solid content of the aqueous monomer solution and the gel solid content) is not less than 1 mass %, further not less than 2 mass %, and particularly not less than 5 mass % and owing to the solid content increase, the water-absorbing resin with high physical properties can be obtained with high productivity and low energy. In the drying step, similarly, increase of the resin solid content not only reduces energy but also causes a preferable effect on decrease of adhesion to the dryer.

From the viewpoint of solid content increase in the drying step, prevention of adhesion of the hydrogel to the dryer, particle size control of a product and the like, the water-absorbing resin fine particles obtained in the classification step can be recycled to the particulated water-containing gel-like crosslinked polymer before drying. The solid content of the particulated water-containing gel-like crosslinked polymer before introduction into the drying step is preferably not less than 45 mass %. The particulated water-containing gel-like crosslinked polymer is dried in a scale of 1 [t/hr] or more. The resin solid content can be controlled based on the monomer concentration, water evaporation at the time of polymerization, recycling of the fine powder and the like, and increase of the resin solid content can not only reduce the energy but also adhesion to the dryer.

(e) Other Steps During Interruption Period

In the continuous drying, the interruption of the drying step is a state where the particulated water-containing gel-like crosslinked polymer or a dried material thereof is not charged to or discharged out of a dryer and as a synonym, it is also a state where the particulated water-containing gel-like crosslinked polymer or a dried material thereof is stopped in a continuous dryer and for example, a state where a belt of a dryer or a paddle (stirring discharge) of a heating treatment apparatus is stopped. As a factor of the above-mentioned phenomena, there are stopping by a trouble in steps following the drying step (a breakdown of the apparatus or adhesion of and blocking with an undried material) and the like, or stopping of the dryer itself to inhibit charging or discharging of the particulated water-containing gel-like crosslinked polymer or a dried material thereof in the dryer from or out of the dryer. In such a case, from the viewpoint of stability of a product, it is preferable to carry out at least some of operable steps following the drying step, for example, a classification step, a storage step, a conveying step, a surface treatment (crosslinking) step, etc., during the interruption period of the drying step.

Further, during the interruption period of the drying step, the steps following the drying step are stopped while being kept in a heated state and thereafter, the respective steps are restarted. Herein, the heated state means that the respective apparatuses are heated regardless of presence or absence of the water-absorbing resin and for example, a classification step, a storage step, a conveying step, a surface-crosslinking step, etc., are stopped while being kept in the heated state. The heating temperature may be properly determined and it is preferably not lower than 50° C., more preferably not lower than 60° C., and still more preferably 80 to 140° C.

(f) Preferable Steps after Drying Step

The present invention involving stopping drying in a heated state also involves a plurality of joined steps, preferably not less than 4 steps, and further not less than 6 steps following the drying step, and concretely, a pulverizing step, a classification step before surface-crosslinking, a surface-crosslinking step, a second classification step after surface-crosslinking, a fine powder recovery step after the classification step, an undried material removal step, a packaging step, and in addition a conveying step for joining these steps (e.g. air conveying step). These steps are exemplified in Patent Documents 1 to 13.

Conventionally, in the case the production process involves a plurality of joined steps after the drying step, if the flow is stopped in only one step in the process, the entire plant has to be stopped and, therefore, there occurs problems that at the time of restarting, the quality is not stable excess energy is required for restarting of the operation and the like, and in the worst case, the operation may be stopped. In addition, a colored foreign matter sometimes causes contamination at the time of restarting. However, the present invention solves the above-mentioned conventional problems by stopping drying in the heated state.

(g) Dry Air

At the time of interruption of the drying step in the present invention, from the viewpoint of retention of physical properties of the water-absorbing resin and suppression of the blocking phenomenon, it is preferable to inject dry air into the dryer during the interruption period of the drying step. The dew point of the air may be not higher than 0° C. (minus dew point), and is preferably −100 to −5° C., more preferably −95 to −30° C., still more preferably −90 to −35° C., and particularly preferably −85 to −40° C. A method for controlling the dew point of the air is not particularly limited and air may be properly dried by using appliances such as a membrane drier, a cooling adsorption type drier, and a diaphragm drier solely or in combination. In the case where a cooling adsorption type drier is used, it may be of heat regeneration manner, a non-heat regeneration manner, or a non-regeneration manner.

(h) Conventional Drying Method

Conventionally, the following Patent Documents 14 to 37 etc. have been proposed as methods for drying a water-absorbing resin; however, none of them discloses an object of the prevent invention and the stopping method of the drying step.

That is, examples known as the method for drying a water-absorbing resin include methods of using a belt type dryer (Patent Documents 14 to 18), a method for thin film drying by a drum drier and the like (Patent Document 19), a method for azeotropic dehydration in an organic solvent (Patent Document 20), a method for drying in a fluidized bed (Patent Document 21), a method for vibrating and fluidizing drying (Patent Document 22), a method for stirring drying with a rotor (Patent Document 23) and the like. As a drying condition for a water-absorbing resin, methods for controlling the dew point and temperature (Patent Documents 24 and 25), a method for roughly crushing during the drying and then stirring drying (Patent Document 26) and the like, are proposed in order to improve physical properties (e.g., decrease of residual monomers, improvement of absorption capacity, and decrease of water-soluble components). Further, since an undried material may be generated because of drying of the water-absorbing resin and an excess load is applied to the pulverizing, methods for removing the undried material (Patent Documents 11 to 13) are also known. In order not to generate an undried material, examples known are a method for defining the fluidity of a polymer gel (Patent Document 27), methods using an apparatus for leveling a gel by a dryer (Patent Documents 28 and 29), a drying method using a special apparatus for quantitatively supplying a gel to a dryer (Patent Document 30), and a method of using infrared rays and the like in addition to hot air (Patent Document 31). In order to improve the drying efficiency, methods of adding a surfactant or inorganic fine particles to a hydrogel (Patent Documents 32 to 36) are also known. A drying method for a hydrogel having a low neutralization content (Patent Document 37) is also proposed.

(Patent Document 14) US Patent Application Publication No. 2008/214749
(Patent Document 15) WO No. 2008/087114 pamphlet
(Patent Document 16) WO No. 2008/037676 pamphlet
(Patent Document 17) Japan Patent Application Publication No. 8-073518
(Patent Document 18) Japan Patent Application Publication No. 7-270070
(Patent Document 19) Japan Patent Application Publication No. 54-053165
(Patent Document 20) Japan Patent Application Publication No. 64-060683
(Patent Document 21) U.S. Pat. No. 6,906,159
(Patent Document 22) Japan Patent Application Publication No. 2001-018222
(Patent Document 23) U.S. Pat. No. 5,005,771
(Patent Document 24) U.S. Pat. No. 4,920,202
(Patent Document 25) U.S. Pat. No. 6,207,796
(Patent Document 26) U.S. Pat. No. 6,187,902
(Patent Document 27) US Patent Application Publication No. 2008/0021150
(Patent Document 28) Japan Patent Application Publication No. 10-059534
(Patent Document 29) U.S. Pat. No. 5,229,487
(Patent Document 30) Japan Patent Application Publication No. 2003-012812
(Patent Document 31) Japan Patent Application Publication No. 2007-224224
(Patent Document 32) Japan Patent Application Publication No. 2000-143720
(Patent Document 33) Japan Patent Application Publication No. 2002-226599
(Patent Document 34) US Patent Application Publication No. 2007/123624
(Patent Document 35) Japan Patent Application Publication No. 2006-160774
(Patent Document 36) U.S. Pat. No. 5,945,495
(Patent Document 37) WO No. 2008/034786 pamphlet (2-4) Pulverizing Step and Classification Step (Particle Size Adjustment after Drying)

These steps are steps for pulverizing and classifying the dried material obtained in the drying step to obtain a water-absorbing resin powder. The water-absorbing resin powder is a water-absorbing resin before the water-absorbing resin is subjected to the following surface-crosslinking treatment. The dried material obtained in the drying step can be used as a dried powder as it is, but the particulated hydrogel may possibly be agglomerated at the time of drying to form block-like agglomerates. This phenomenon is observed particularly in a band dryer and pulverizing or rough crushing (break into small pieces) is needed. Further, in order to improve the physical properties in the surface-crosslinking step described later, it is preferable to control the water-absorbing resin powder to have a specified particle size. The particle size may be properly controlled not only in the pulverizing step and classification step but also in the polymerization step (particularly, reverse-phase suspension polymerization), the fine powder recovery step, the granulation step, etc. Hereinafter, the particle size is defined by a standard sieve (JIS Z8801-1 (2000)).

A pulverizer to be used in the pulverizing step is not particularly limited and conventionally known pulverizers may be used. Specific examples thereof include a roll mill, a hammer mill, a roll granulator, a jaw crusher, a gyrectory crusher, a cone crusher, a roll crusher, a cutter mill, etc. Among them, a multi-stage roll mill or a roll granulator is preferably used from the viewpoint of particle size control. In the classification step, various kinds of classification apparatuses such as sieving classification and air current classification can be used.

The classification step in the present invention is carried out inevitably before surface-crosslinking and/or after surface-crosslinking, preferably before surface-crosslinking, and still more preferably carried out twice in total before surface-crosslinking and after surface-crosslinking.

From the viewpoint of improvement of physical properties of a water-absorbing resin to be obtained in this step, it is preferable to control the particle size to be in the following range. That is, the mass average particle diameter (D50) of the water-absorbing resin powder (before surface-crosslinking) is preferably 200 to 600 more preferably 200 to 550 μm, still more preferably 250 to 500 μm, and particularly preferably 350 to 450 μm. The ratio of fine particles which pass through a sieve with meshes of 150 μm (JIS standard sieve) is preferably 0 to 5 mass %, more preferably 0 to 3 mass %, and still more preferably 0 to 1 mass % relative to the entire water-absorbing resin powder. The ratio of coarse particles which do not pass through a sieve with meshes of 850 μm (JIS standard sieve) is preferably 0 to 5 mass %, more preferably 0 to 3 mass %, and still more preferably 0 to 1 mass % relative to the entire water-absorbing resin powder. The particle size is measured by a method disclosed in WO No. 2004/69915 and EDANA-ERT 420.2.-02 (Particle Size Distribution).

(2-5) Surface Treatment Step

In the present invention, a step for reforming the periphery of particle surface for the water-absorbing resin powder with the prescribed particle size is called as a surface treatment step. Herein, the "surface treatment" may be surface-crosslinking and also addition of various kinds of additives and polymers to the particle surface and preferably, surface-crosslinking by a thermal reaction is indispensably carried out. The surface treatment other than surface-crosslinking may be addition of a water-soluble or water-insoluble polymer, a lubricant, a chelating agent, a deodorant, an antibacterial agent, water, a surfactant, water-insoluble fine particles, an antioxidant, a reducing agent, etc. These agents may be added and mixed in an amount of preferably 0 to 30 mass % and more preferably 0.01 to 10 mass % to the water-absorbing resin powder or water-absorbing resin particles after surface-crosslinking. These agents may be mixed and heated up to the above-mentioned upper limit in place of the following surface-crosslinking agent. Hereinafter, a surface-crosslinking step is explained as a representative and the following respective steps of mixing, heating, and stopping can be properly be applied for the surface treatment step, which is a superordinate concept.

(a) Mixing Step (Surface-Crosslinking Step)

In the present invention, in order to improve the water absorption performance, preferably a surface-crosslinking step is further involved. In the present invention, coloration is scarcely caused and a whiter water-absorbing resin can be obtained by the surface-crosslinking treatment. The following respective steps can be applied preferably for surface-crosslinking of a water-absorbing resin, particularly for high temperature surface-crosslinking.

The surface-crosslinking step in the present invention is composed of a step of mixing a water-absorbing resin powder with a surface-crosslinking agent, a step of heating treatment for the mixture, and a cooling step carried out if necessary.

(Covalent Bonding Surface-Crosslinking Agent)

A surface-crosslinking agent to be used for the present invention is not particularly limited and various kinds of organic and inorganic surface-crosslinking agents can be mentioned. Among them, an organic surface-crosslinking agent alone or combination use of an organic surface-crosslinking agent and an ion bonding surface-crosslinking agent is preferable. A covalent bonding surface-crosslinking agent is preferably used as the organic surface-crosslinking agent, preferable examples to be used are dehydration reactive surface-crosslinking agents such as polyhydric alcohol compounds, epoxy compounds, polyamine compounds and their condensation products with haloepoxy compounds, oxazoline compounds (mono-, di-, or poly-) oxazolidinone compounds, alkylene carbonate compounds. Particularly dehydration reactive surface-crosslinking agents such as a polyhydric alcohol compound, an alkylene carbonate compound, and an oxazolidinone compound, which require high temperature reaction are preferably used. More concretely, examples are compounds exemplified in U.S. Pat. Nos. 6,228, 930, 6,071,976, 6,254,990, etc. Examples are dehydration esterification reactive surface-crosslinking agents include polyalcohol compounds such as mono-, di-, tri-, or tetra-propylene glycol, 1,3-propanediol, glycerin, 1,4-butanediol, 1,3-butanediol, 1,5-pentanediol, 1,6-hexanediol and sorbitol; epoxy compounds such as ethylene glycol diglycidyl ether and glycidol; alkylene carbonate compounds such as ethylene carbonate; oxetane compounds; cyclic urea compounds such as 2-imidazolidinone; and the like. One or more kinds of covalent surface-crosslinking agents (particularly, dehydration reactive surface-crosslinking agents) can be used in combination. The use amount of the surface-crosslinking agents may be properly determined in a range of preferably 0.001 to 10 parts by mass and more preferably 0.01 to 5 parts by mass relative to 100 parts by mass of the water-absorbing resin powder.

(Ion Bonding Surface-Crosslinking Agent)

In the present invention, from the viewpoint of improvement of physical properties such as liquid permeability, an inorganic surface-crosslinking agent can be used other than the organic surface-crosslinking agent. Examples usable as the inorganic surface-crosslinking agent is not particularly limited and may include divalent or higher, preferably, trivalent to tetravalent polyvalent metal salts (organic salts and inorganic salts) or hydroxides. Concretely, polyvalent metals to be used are aluminum, zirconium, etc., and aluminum lactate and aluminum sulfate are usable. These inorganic surface-crosslinking agents may be used simultaneously with or separately from the organic surface-crosslinking agent. The surface-crosslinking with polyvalent metals is exemplified in International Publication Nos. 2007/121037, 2008/09843, and 2008/09642, in U.S. Pat. Nos. 7,157,141, 6,605, 673, and 6620889, in US Patent Application Publication Nos. 2005/0288182, 2005/0070671, 2007/0106013, 2006/0073969, etc. One or more kinds of ion bonding surface-crosslinking agents can be used in combination. The use amount may be properly determined in a range of preferably 0.001 to 10 parts by mass and more preferably 0.01 to 5 parts by mass relative to 100 parts by mass of the water-absorbing resin powder.

In the present invention, from the viewpoint of improvement of physical properties such as liquid permeability, a polyamine polymer may be used simultaneously or separately in addition to the organic surface-crosslinking agent. A polyamine polymer having a mass average molecular weight of about 5000 to 1000000 is particularly preferably used, and examples are exemplified in U.S. Pat. No. 7,098,284, WO Nos. 2006/082188, 2006/082189, 2006/082197, 2006/111402, 2006/111403, 2006/111404, etc.

The present invention can provide a water-absorbing resin with high whiteness even by high temperature heating or drying with air (hot air) which conventionally causes intense coloration. In the case of aiming at providing particularly a sanitary material (especially a paper diaper), it is preferable to improve the absorption capacity under load (AAP) described later to the following range, preferably not less than 20 g/g by a surface-crosslinking treatment.

At the time of mixing the surface-crosslinking agent, water is preferably used as a solvent. The use amount of water may be properly determined in a range of preferably 0.5 to 20 parts by mass and more preferably 0.5 to 10 parts by mass relative to 100 parts by mass of the water-absorbing resin powder. A hydrophilic organic solvent may be used in combination if necessary, other than water, and its use amount may be properly determined in a range of preferably 0 to 10 parts by mass and more preferably 0 to 5 parts by mass relative to 100 parts by mass of the water-absorbing resin powder.

Further, at the time of mixing a surface-crosslinking agent solution, a water-insoluble fine particle powder and a surfactant are allowed to coexist to an extent that the effect of the present invention is not hindered. The types, the use amount and the like, of the water-insoluble fine particle powder and surfactant are described in, for example, U.S. Pat. No. 7,473,739 etc. and the use amount may be properly determined in a range of preferably 0 to 10 parts by mass, more preferably 0 to 5 parts by mass, and still more preferably 0 to 1 part by mass relative to 100 parts by mass of the water-absorbing resin powder.

(b) Heating Treatment Step

In the surface-crosslinking step, after the water-absorbing resin powder and a surface-crosslinking agent are mixed, the mixture is preferably subjected to a heating treatment and thereafter to a cooling treatment if necessary. A conventionally known dryer is used for the heating treatment and the above-mentioned stopping method of the present invention is preferably applied. The heating temperature (which is a heat medium temperature or a material temperature, particularly a material temperature) at the time of the heating treatment may be properly determined in accordance with the type, amount and the like, of the surface-crosslinking agent to be used and it is preferably 70 to 300° C., more preferably 120 to 250° C., still more preferably 150 to 250° C., and particularly preferably 170 to 230° C. In the case a dehydration reactive surface-crosslinking agent is used, the heating temperature is preferably 150 to 250° C. and more preferably 170 to 230° C. In the case the treatment temperature is lower than 70° C., the heating treatment time is extended and it results in decrease of the productivity and further it becomes impossible to form a uniform surface-crosslinked layer and, therefore, it is not preferable. In the case the treatment temperature exceeds 300° C., the water-absorbing resin powder is deteriorated and, therefore, it is not preferable. The heating time for the heating treatment is preferably in a range of 1 minute to 2 hours. The heating treatment can be carried out in a common dryer or a heating furnace. The methods of surface-crosslinking described in EP Patent Nos. 0349240, 0605150, 0450923, 0812873, 0450924, 0668080, Japan Patent Application Publication Nos. 7-242709, 7-224304, U.S. Pat. Nos. 5,409,771, 5,597,873, 5,385,983, 5,610,220, 5,633,316, 5,674,633, 5,462,972, WO Nos. 99/42494, 99/43720, 99/42496, etc. can be employed preferably in the present invention.

(Heating Treatment Apparatus)

Various kinds of heating treatment apparatuses such as a fluidized bed heating treatment apparatus, a belt type heating treatment apparatus, a paddle type heating treatment apparatus, a disk type heating treatment apparatus, a hot air heating treatment apparatus, an infrared heating treatment apparatus can be used as the heating treatment apparatus of the present invention. Among them, a paddle type heating treatment apparatus is preferable and a disk type heating treatment apparatus is particularly preferable. Specific examples thereof include a Bepex-heating treatment apparatus and a Nara-heating treatment apparatus. In this description, for convenience, the term "heating treatment apparatus" is employed, but it is same as a dryer. The heating treatment can be carried out by heating a jacket or blowing hot air in the heating treatment apparatus itself. A dryer connected successively, for example, a box type dryer, a rotary tubular furnace, or a heatable screw is also proper.

(c) Cooling Step

This step is a step carried out arbitrarily after the heating treatment step. In the case a dehydration reactive crosslinking agent made from a polyhydric alcohol compound, an alkylene carbonate compound, and an oxazolidinone compound, which require high temperature reaction, is used in the heating treatment step, the cooling step is preferably carried out.

A cooling apparatus to be used in the cooling step is not particularly limited and an apparatus having the same configuration as the apparatus used for the heating treatment step can be used. That is, the apparatus may be the transverse type continuous stirring apparatus or the apparatus described in U.S. Pat. No. 7,378,453 etc. For example, a biaxial stirring apparatus in which cooling water is circulated in the inner wall or other heat transfer surfaces and the like, can be used. The temperature of the cooling water is adjusted to be lower than the heating treatment temperature in the surface treatment step and may be properly determined in a range of preferably not lower than 25° C. and lower than 70° C.

(2-6) Fine Powder Recycling Step

The fine powder recycling step in the present invention is a step of recycling a fine powder (particularly, a fine powder containing particles not larger than 150 μm as a main component in an amount of particularly not less than 70 mass %) obtained by drying and if necessary pulverizing and classification to the polymerization step or the drying step after separation as it is or after hydration. For example, methods described in US Patent Application Publication No. 2006/247351, U.S. Pat. No. 6,228,930 etc. can be employed.

The particle size can be controlled by adding the recycled fine powder and additionally, a high solid content, which is indispensable in the present invention, can be easily be achieved by adding a water-absorbing resin powder and further, and an addition of the fine powder makes separation of the water-absorbing resin from a drying belt after drying easy and, therefore, it is preferable.

Regarding a water-absorbing resin obtained by a production process involving a fine powder recycling step, in a conventional production process, because of uneven drying due to the addition of the fine powder, increase of residual monomers, decrease of absorption capacity, and the like, it has been difficult to obtain a water-absorbing resin with high physical properties. On the other hand, in the production process of the present invention, particularly in the case the process for producing a water-absorbing resin involves the fine powder recycling step, the process is excellent in the effect of preventing physical property deterioration and preventing coloration. That is, it is preferable that the solid content of the hydrogel is increased to not less than 45 mass %, not less than 50 mass %, not less than 55 mass %, and not less than 60 mass % by evaporating water or adding a water-absorbing resin fine powder in the polymerization step. The increase of the solid content from the monomer (solid content of hydrogel after polymerization—mass % of monomer before polymerization) is preferably not less than 1 mass %, further 2 to 40 mass %, and particularly preferably in a range of 3 to 30 mass %. It is also preferable to add a step of recycling the water-absorbing resin fine powder after drying or its moisturized product to the polymerization step or drying step.

(2-7) Other Steps (and Stopping of Heating)

Besides the above-mentioned drying step, if necessary, a surface treatment step for a polyvalent metal salt, a recycling step of the evaporated monomer, a granulation step, a fine powder removal step, etc. may be provided. In order to cause an effect for color stabilization with time, prevent gel deterioration and the like, the above-mentioned additives may be added to some or all of the respective steps if necessary. The production process of the present invention preferably involves the fine powder recycling step.

During polymerization or after polymerization, a water-soluble or water-insoluble polymer, a lubricant, a chelating agent, a deodorant, an antibacterial agent, water, a surfactant, water-insoluble fine particles, an antioxidant, a reducing agent, etc. may be added and mixed in an amount of 0 to 30 mass % and further about 0.01 to 10 mass % to the water-absorbing resin particles. These additives may also be used as a surface treatment agent.

One or more steps such as a conveying step, a storage step, a packaging step, and an addition step of adding other additives (fine particles, a deodorant, an antibacterial agent, etc.) may also be preferably carried out. These steps are described in Patent Documents 1 to 10 etc. and the stopping after the drying step is carried out in the heated state, preferably at not lower than 50° C. and further not lower than 60° C. The upper limit of the heating temperature is not higher than 140° C., further not higher than 120° C., and particularly not higher than 100° C., from the viewpoint of the cost and coloration. The above-mentioned minus dew point is also preferably employed. The stopping of these steps means a state where an apparatus is unused, that is, a state where the water-absorbing resin is substantially absent and the water-absorbing resin is not supplied to and discharged out of an apparatus in each step.

That is, in the present invention, the drying step is stopped in a heated state; preferably, the drying step and the surface treatment step (especially the surface-crosslinking step) are stopped in a heated state; and more preferably, other steps (especially all steps) after the drying step in addition to the drying step and the surface treatment step (especially the surface-crosslinking step) are stopped in a heated state. It is made possible to restart operation without any trouble and carry out stable operation by stopping in the heated state.

[3] Physical Properties of Water-Absorbing Resin

The water-absorbing resin of the present invention contains a polyacrylic acid (salt)-type water-absorbing resin as a main component and obtained by the above-mentioned polymerization method, surface-crosslinking method, and the like, in the case where the water-absorbing resin is used for sanitary goods, particularly paper diapers. The obtained water-absorbing resin is preferable to control at least one of the following (3-1) to (3-6), further two or more including AAP, and particularly three or more. In the case the water-absorbing resin does not satisfy the following respective physical properties, there is a possibility that high concentration diapers containing not less than 40 mass % of the water-absorbing resin cannot sufficiently exhibit the performance.

(3-1) CRC (Absorption Capacity without Load)

The CRC (absorption capacity without load) of the water-absorbing resin to be obtained by the present invention is preferably 10 [g/g] or higher, more preferably 20 [g/g] or higher, still more preferably 25 [g/g] or higher, and particularly preferably 30 [g/g] or higher. The upper limit of the CRC is not particularly limited, is preferably 50 [g/g] or lower, more preferably 45 [g/g] or lower, still more preferably 40 [g/g] or lower. In the case the CRC is lower than 10 [g/g], the water absorption amount of the water-absorbing resin is small and the water-absorbing resin is possibly unsuitable for use for an absorbent body in sanitary goods such as paper diapers. In the case the CRC exceeds 50 [g/g], if the water-absorbing resin is used for such an absorbent body, it may possibly become impossible to obtain sanitary goods excellent in liquid intake speed and, therefore, it is not preferable. The CRC can be properly controlled by the above-mentioned internal crosslinking agent, surface-crosslinking agent and the like.

(3-2) AAP (Absorption Capacity Under Load)

The AAP (absorption capacity under load) of the water-absorbing resin to be obtained by the present invention is preferably not lower than 20 [g/g], more preferably not lower than 22 [g/g], and still more preferably not lower than 24 [g/g] at a pressure of 4.83 kPa (0.7 psi) by employing the drying as an accomplishing means in order to prevent leakage in paper diapers. The upper limit of the AAP is not particularly limited; however, from the viewpoint of balance with other physical properties, it is preferably not higher than 40 [g/g]. In the case the AAP is lower than 20 [g/g], if the water-absorbing resin is used for an absorbent body, it may possibly become impossible to obtain sanitary goods with little liquid return (generally, also referred to as "Re-Wet") at the time a pressure is applied to the absorbent body and it is not preferable. The AAP can be properly controlled by the above-mentioned surface-crosslinking agent, the particle size, etc.

(3-3) SFC (Saline Flow Conductivity)

The SFC (saline flow conductivity) of the water-absorbing resin to be obtained by the present invention, which is a liquid permeability under pressure, is preferably 1 [$\times 10^{-7} \cdot cm^3 \cdot s \cdot g^{-1}$] or higher, more preferably 10 [$\times 10^{-7} \cdot cm^3 \cdot s \cdot g^{-1}$] or higher, still more preferably 50 [$\times 10^{-7} \cdot cm^3 \cdot s \cdot g^{-1}$] or higher, particularly preferably 70 [$\times 10^{-7} \cdot cm^3 \cdot s \cdot g^{-1}$] or higher, and most preferably 100 [$\times 10^{-7} \cdot cm^3 \cdot s \cdot g^{-1}$] or higher by employing the drying as an accomplishing means in order to prevent leakage in paper diapers. The upper limit of the SFC is not particularly limited; however, from the viewpoint of balance with other physical properties, it is preferably not higher than 3000 [$\times 10^{-7} \cdot cm^3 \cdot s \cdot g^{-1}$], more preferably not higher than 2000 [$\times 10^{-7} \cdot cm^3 \cdot s \cdot g^{-1}$]. In the case the SFC exceeds 3000 [$\times 10^{-7} \cdot cm^3 \cdot s \cdot g^{-1}$], if the water-absorbing resin is used for such an absorber, liquid leakage may possibly occur in the absorber and, therefore, it is not preferable. The SFC can be properly controlled by the above-mentioned drying method and the like.

(3-4) EXT (Amount of Water Soluble Components)

The EXT (amount of water soluble components) of the water-absorbing resin to be obtained by the present invention is preferably 35 mass % or lower, more preferably 25 mass % or lower, still more preferably 15 mass % or lower, and particularly preferably 10 mass % or lower. In the case the Ext exceeds 35 mass %, the water-absorbing resin to be obtained may possibly become weak in the gel strength and inferior in the liquid permeability. If such a water-absorbing resin is used for an absorber, it may possibly become impossible to obtain a water-absorbing resin with little liquid return (re-wet) at the time a pressure is applied to the absorber and it is not preferable. The Ext can be properly controlled by the above-mentioned internal crosslinking agent and the like.

(3-5) Residual Monomer

The residual Monomer amount of the water-absorbing resin to be obtained by the present invention, from the viewpoint of safety, is controlled to be preferably 0 to 400 ppm, more preferably 0 to 300 ppm, still more preferably 0 to 200 ppm. The residual monomer amount is controlled by the above-mentioned polymerization method and the like.

(3-6) Initial Color Hue

The water-absorbing resin to be obtained by the present invention is excellent in the initial color hue. The color hue (initial color hue) of a water-absorbing resin immediately after production obtained by the present invention shows the following numerical value. The initial color hue means the color hue immediately after production and in general, it is the color hue measured before shipment from a plant. It is also a value measured within 1 year from the production in the case of preservation in an atmosphere at not higher than 30° C. and a relative humidity of not higher than 50% RH. Concretely, in a Hunter Lab system, the L value (Lightness) is preferably not lower than 85, more preferably not lower than 87, and still more preferably not lower than 89. The b value is preferably −5 to 10, more preferably −5 to 9, still more preferably −4 to 8, and particularly preferably −1 to 7. The a value is preferably −2 to 2, more preferably −1 to 1, still more preferably −0.5 to 1, and particularly preferably 0 to 1. As another chromaticity, YI (Yellow Index) value is preferably not higher than 10, more preferably not higher than 8, and particularly preferably not higher than 6. As another chromaticity, the WB (White Balance) value is preferably not lower than 70, more preferably not lower than 75, and particularly preferably not lower than 77. The water-absorbing resin obtained by the present invention is excellent in coloration with time and shows sufficient whiteness in an accelerating test carried out in high temperature and high humidity.

[4] Use of Water-Absorbing Resin

Use of the water-absorbing resin obtained by the production process of the present invention is not particularly limited and the water-absorbing resin may be used for absorbing articles including sanitary goods such as paper diapers, sanitary napkins, and pads for incontinent, water retention agents for agriculture and horticulture, solidifying agents for waste liquids, industrial water shielding materials, and the like.

EXAMPLES

Hereinafter, the present invention will be described in detail with reference to examples and comparative examples; however, the present invention should not be construed in a limited way based on the description of the examples. For convenience, "litter" is expressed as "L" and "mass %" as "wt %" in some cases. The various physical properties described in CLAIMS and Examples of a water-absorbing resin obtained by the present invention were measured according to EDANA method and the following measurement examples under the condition of room temperature (20 to 25° C.) and a humidity of 50% RH unless otherwise specified.

1. Initial Color Hue and Coloration with Time

The initial color hue and coloration with time of a water-absorbing resin of the present invention were measured according to measurement methods described in WO No. 2009/005114 pamphlet.

2. Resin Solid Content (Solid Content)

A water-absorbing resin in an amount of 1.00 g was weighed in an aluminum cup with a bottom surface diameter of about 50 mm and the total weight W1 [g] of the sample (the water-absorbing resin and the aluminum cup) was accurately weighed.

Next, the sample was stood still in an oven at an atmosphere temperature of 180° C. and the water-absorbing resin was dried. After 3 hours, the sample in the aluminum cap was taken out of the oven and cooled to room temperature in a desiccator. Thereafter, the total weight W2 [g] of the sample (the water-absorbing resin and the aluminum cup) after drying was measured and the solid content (unit; [mass %]) was calculated according to the following expression.

Solid content[wt/%]=100−{(W1-W2)/(weight of water-absorbing resin[g])×100} [Mathematic 1]

In the case of measuring the resin solid content of a particulated water-containing gel-like crosslinked polymer (particulated hydrogel), the sampling amount of the particulated hydrogel was changed to be 2 to 4 g and the drying time was changed to be 24 hours.

3. SFC (Saline Flow Conductivity)

The SFC (saline flow conductivity) of the water-absorbing resin to be obtained by the present invention was measured according to the description in the specification of U.S. Pat. No. 5,669,894.

4. Other Physical Properties

The physical properties of a water-absorbing resin to be obtained by the present invention, that is, CRC (absorption capacity without load), particle size distribution, pH soluble matter, remaining acrylic acid amount, and the like, were measured according to ERT of EDANA or the description in the specification of US Patent Application Publication No. 2006/204755.

Comparative Example 1

Continuous production of a water-absorbing resin was carried out by joining a continuous polymerization step, a drying step by a band dryer, a pulverizing step, and a classification step.

That is, 0.04 g of sodium persulfate (relative to 1 mol of monomer) and 100 ppm of diethylenetriamine pentaacetic acid pentasodium salt were continuously mixed by line mixing with an aqueous solution of acrylic acid sodium salt partially neutralized in an amount of 70 mol % (monomer concentration: 53 mass %) containing 0.03 mol % (based on monomer) of polyethylene glycol diacrylate (average molecular weight: 478) as an internal crosslinking agent and the mixture was supplied to a belt polymerization apparatus and subjected to aqueous solution polymerization. The hydrogel obtained in this manner was finely crushed by a vertical crusher (manufactured by Orient Co., Ltd., screen of 12 mm) to obtain a particulated water-containing gel-like polymer (1) containing 70 mass % of solid content and having fluidity.

The particulated water-containing gel-like polymer (1) was continuously layered by using a traverse feeder for a continuous air ventilating belt type dryer on a punching metal of a continuous air ventilating belt which was continuously operated by controlling the sequence of the traverse feeder and continuously dried on the ventilating belt for 35 minutes. The discharge amount (treatment amount) of the dried material was 1.7 [t/hr]. The dying apparatus and drying condition were as shown in the following (a) to (c).

(a) Belt Type Dryer

A dryer used was a continuous air ventilating dryer having 6 drying chambers in total which can independently adjust the hot air temperature and which have the same size and in which an air ventilating belt passes. The hydrogel passed in about 5.8 minutes (=35 min/6 chambers on the belt) in the respective 6 drying chambers.

(b) Hot Air Temperature and Linear Velocity

The hot air temperature of the drying chambers was controlled to be 180° C. by adjusting the steam flow rate of a heat exchanger and the linear velocity of the hot air was set to be 1.6 m/s. The blow direction of the first chamber was upward from the bottom surface and the blow direction of the second to the sixth chambers was set downward to the bottom surface from an upper part of the dryer.

(c) Air Ventilating Belt

The air ventilating belt used was a stainless steel belt (band) made of SUS 304 and having long round holes with a width of 1.2 mm and a length of 15 mm in a zigzag arrangement and a hole ratio of 27%. The particulated water-containing gel-like polymer was agglomerated like blocks after drying. After loosened agglomerated blocks after drying into several millimeters, the entire amount of the loosened dried product was continuously supplied to a roll mill (roll gaps: 1.0 mm/0.55 mm/0.42 mm from the upper side) and pulverized and classified with a sieving apparatus having a metal sieving net with meshes of 850 µm to obtain a comparative water-absorbing resin (1).

After the continuous polymerization and continuous drying and the pulverizing classification were carried out continuously for 60 days, operation of all of the apparatuses including the heating of the dryer (hot air at 180° C.) was stopped for 48 hours in order to change the product to a product with 0.1 mol % of an internal crosslinking agent. After 48 hours, the atmosphere temperature in the dryer was increased from room temperature (25° C.) to 180° C. and then the continuous operation was restarted to continuously produce a water-absorbing resin with 0.1 mol % of an internal crosslinking agent. In this case, a colored foreign matter (colored water-absorbing resin) was partially mixed at the beginning of the restarted operation and an excess load (increase of power consumption) on the drying belt was found at the time of restarting of the operation and abnormal noise was generated at the time of rotation of the stainless steel band type dryer.

Example 1

In Comparative Example 1, the atmosphere temperature was changed to be 120° C. during the time of stopping the dryer. The same operation was carried out as the operation in Comparative Example 1, except that at the time of stopping continuous production, the temperature of the dryer (the atmosphere temperature of the drying chambers) was adjusted to be from 180° C. to 120° C. by adjusting the steam flow rate and after 48 hours from the stopping of the steps, the atmosphere temperature in the dryer was increased from 120° C. to 180° C. and the continuous operation was restarted. When a water-absorbing resin with 0.1 mol % of the internal crosslinking agent was continuously produced, no foreign matter was mixed at the beginning of restarted operation and no excess load (increase of power consumption) on the drying belt was observed at the time of operation.

Comparative Example 2

Polymerization and drying were stopped because of a trouble of a pulverizer during the continuous production of Comparative Example 1. Since the latter half of the pulverizing step was stopped, the steps before the pulverizing step were also stopped. The stopping of the polymerization led to stopping of monomer supply and stopping of drying led to stopping of rotation of the belt (band) on which the hydrogel was set, and stopping of heating.

After the trouble of the pulverizer was solved, the atmosphere temperature in the dryer was increased from room temperature (25° C.) to 180° C. after 24 hours and then the continuous operation was restarted; however, an excess load was applied on the drying belt at the time of restarting of the operation and abnormal noise was generated from the band type dryer. Further, a dried material (agglomerates of particulate dried material) was not separated from the dryer.

Example 2

In Comparative Example 2, as to the stopping of the drying, the rotation of the belt (band) on which the hydrogel was set was stopped and the temperature of the dryer was controlled to be 80° C. by adjusting the steam flow rate. After the trouble of the pulverizer was solved, the atmosphere temperature in the dryer was increased from 80° C. to 180° C. after 24 hours and then the continuous operation was restarted, and no load was applied on the drying belt at the time of restarting of the operation and no abnormal noise was generated from the band type dryer. Further, a dried material (agglomerates of particulate dried material) was sufficiently separated from the dryer.

Example 3

In Comparative Example 2, the dryer was stopped while keeping the temperature thereof at 180° C. After the trouble of the pulverizer was solved, the continuous operation was restarted while the atmosphere temperature in the dryer was being kept at 180° C. after 24 hours, and no load was applied on the drying belt at the time of restarting of the operation and no abnormal noise was generated from the band type dryer. Further, a dried material (agglomerates of particulate dried material) was sufficiently separated from the dryer. The obtained water-absorbing resin was partially yellowed and the absorption capacity was slightly lowered. The hot air heated by steam was reheated and reused after discharged out of the dryer.

Example 4

In Comparative Example 1, the dryer was stopped for 10 days while being kept in a state of heated at 120° C. by adjusting the steam flow rate and during the time, the classification step and the pulverizing step were subjected to periodic repair. Thereafter, the heating of the dryer was stopped. After it was confirmed that the temperature of the drying chambers was lowered to room temperature (25° C.) after 24 hours, cleaning of the water-absorbing resin retained in the dryer or its lower part was started. The water-absorbing resin in the dryer was removed easily and thereafter, operation was restarted. The hot air heated by steam was reheated and reused after discharged out of the dryer.

Comparative Example 3

In Example 4, the dryer was completely stopped. During the dryer was stopped for 10 days at room temperature (temperature difference between night and day: 10 to 35° C.), the classification step and the pulverizing step were subjected to periodic repair. Thereafter, the water-absorbing resin retained in the dryer or its lower part was cleaned. The water-absorbing resin in the dryer adhered to the inner wall and belt of the dryer and was difficult to be removed.

TABLE 1

| | Stopped apparatus | Temperature of stopping [° C.] | Period of stopping [hr] | Excess load at restarting | Abnormal noise | Foreign matter |
|---|---|---|---|---|---|---|
| Comparative Example 1 | Ventilating belt type dryer | Room Temperature | 48 | Found | Generated | Generated |
| Example 1 | ↑ | 120 | ↑ | None | None | None |
| Comparative Example 2 | ↑ | Room Temperature | 24 | Found | Generated | Generated |
| Example 2 | ↑ | 80 | ↑ | None | None | None |
| Example 3 | ↑ | 180 | ↑ | None | Generated | Partially yellowed |
| Example 4 | ↑ | 120 | 240 | None | None | None |
| Comparative Example 3 | ↑ | Room Temperature | ↑ | Found | Generated | Generated |

As shown in Table 1, continuous production (preferably not shorter than 10 days) of a water-absorbing resin in a huge scale (preferably not less than 1 [t/hr]) is made possible by stopping the dryer in a heated state and then restarting the operation. The conventional production processes described in Patent Documents 1 to 13 and drying methods described in Patent Documents 14 to 37 do not at all imply the stopping method of the present invention and its effect.

INDUSTRIAL APPLICABILITY

A water-absorbing resin free from coloration and a foreign matter can be produced economically and stably by continuous production in a huge scale (e.g., 1 [t/hr] or more) and the water-absorbing resin of the present invention can be used for various kinds of sanitary materials such as paper diapers and sanitary napkins and also for various applications.

The invention claimed is:

1. A process for producing a water-absorbing resin, comprising a polymerization step of polymerizing an aqueous unsaturated monomer solution and a drying step of drying a particulated water-containing gel-like crosslinked polymer obtained in a finely crushing step during the polymerization or after the polymerization, wherein
the drying step is carried out by supplying the particulate water-containing gel-like crosslinked polymer to an air ventilating band type continuous dryer and removing the resulting dried polymer from the dryer,
the drying step is interrupted with the dryer kept in a heated state and thereafter the drying step is restarted, and the particulated water-containing gel-like crosslinked polymer is supplied to the dryer after the interruption,
the temperature of the dryer during the interruption time of the drying step is 80 to 140° C., and
the interruption of the drying step means a state where the particulated water-containing gel-like crosslinked polymer or a dried material thereof is taken out of the dryer in an amount of not less than 95 mass % based on the entire retention capacity of the dryer, or not charged to or not discharged out of the dryer in the continuous drying during the interruption.

2. The production process according to claim 1, wherein the drying step is continuous drying.

3. The production process according to claim 1, wherein the interruption time of the drying step is not shorter than 0.5 hours and within 100 days.

4. The production process according to claim 1, wherein the temperature of the dryer during the interruption time of the drying step is lower than the drying temperature by 10° C. or more and not lower than 40° C.

5. The production process according to claim 1, wherein a gas having a dew point of −100 to −5° C. is injected into the dryer during the interruption time of the drying step.

6. The production process according to claim 1, wherein the drying step is continuous drying for not shorter than 24 hours.

7. The production process according to claim 1, wherein the solid content of the particulated water-containing gel-like crosslinked polymer before the drying is not less than 45 mass %.

8. The production process according to claim 1, wherein the particulated water-containing gel-like crosslinked polymer is dried at not less than 1 t/hr in the drying step.

9. The production process according to claim 1, wherein heating of the dryer during the interruption time of the drying step is carried out by heated steam or hot air.

10. The production process according to claim 9, wherein the heated steam is recycled.

11. The production process according to claim 1, further comprising, after the drying step and if necessary, a pulverizing step, a classification step before surface-crosslinking, a surface-crosslinking step, a second classification step after the surface-crosslinking, and a fine powder recovery step after the classification step.

12. The production process according to claim 1, wherein at least some steps after the drying step are carried out during the interruption time of the drying step.

13. The production process according to claim 1, wherein the steps after the drying step are interrupted while the apparatuses used in the steps after the drying step being kept in the heated state and thereafter, the steps after the drying step are restarted.

14. The production process according to claim 1, wherein the polymerization step is continuous kneader polymerization or continuous belt polymerization while vaporizing water.

15. The production process according to claim 1, wherein the water-absorbing resin fine particles obtained in a classification step are recycled to the particulated water-containing gel-like crosslinked polymer before the drying.

16. A process for producing a water-absorbing resin comprising a polymerization step of polymerizing an aqueous unsaturated monomer solution and a drying step of drying a particulated water-containing gel-like crosslinked polymer obtained in a finely crushing step during the polymerization or after the polymerization, wherein
- the drying step is carried out by supplying the particulated water-containing gel-like crosslinked polymer to an air ventilating band type continuous dryer and removing the resulting dried polymer from the dryer,
- the drying step is interrupted and heating of the dryer is stopped, then cleaning of the inside of the dryer is started within 100 hours and thereafter the drying step is restarted, and the particulated water-containing gel-like crosslinked polymer is supplied to the dryer after the interruption,
- the temperature of the dryer during the interruption time of the drying step is 80 to 140° C., and
- the interruption of the drying step means a state where the particulated water-containing gel-like crosslinked polymer or a dried material thereof is taken out of the dryer in an amount of not less than 95% mass based on the entire retention capacity of the dryer, or not charged to or not discharged out of the dryer in continuous drying during the interruption.

* * * * *